(12) United States Patent
Schwirian et al.

(10) Patent No.: US 8,832,883 B2
(45) Date of Patent: Sep. 16, 2014

(54) PATIENT SUPPORT SYSTEMS

(75) Inventors: Jay Schwirian, Monongahela, PA (US); Tushar Shah, Newtown Square, PA (US); Bradley Yakam, New Albany, OH (US)

(73) Assignee: American Home Health Care, Inc., Columbus, OH (US)

( * ) Notice: Subject to any disclaimer, the term of this patent is extended or adjusted under 35 U.S.C. 154(b) by 22 days.

(21) Appl. No.: 13/158,830

(22) Filed: Jun. 13, 2011

(65) Prior Publication Data

US 2011/0302719 A1 Dec. 15, 2011

Related U.S. Application Data

(60) Provisional application No. 61/354,214, filed on Jun. 12, 2010.

(51) Int. Cl.
```
A47C 27/08    (2006.01)
A61B 5/00     (2006.01)
A61G 7/057    (2006.01)
A61B 5/11     (2006.01)
```

(52) U.S. Cl.
CPC ..... *A61G 7/05769* (2013.01); *A61B 2562/0257* (2013.01); *A61G 2203/34* (2013.01); *A61B 5/6891* (2013.01); *A61B 2562/043* (2013.01); *A61B 2562/029* (2013.01); *A61B 2562/0271* (2013.01); *A47C 27/083* (2013.01); *A61B 5/1115* (2013.01); *A61B 5/6892* (2013.01); *A61B 2562/0247* (2013.01); *A47C 27/082* (2013.01); *A61G 2007/05792* (2013.01)
USPC ............................ 5/706; 5/710; 5/713; 5/714

(58) Field of Classification Search
CPC .... A47C 27/08; A47C 27/081; A47C 27/082; A47C 27/087; A47C 27/04; A47C 27/05; A47C 27/066; A47C 27/083; A61G 7/05769
USPC ............................ 5/706, 109, 710–712, 717
See application file for complete search history.

(56) References Cited

U.S. PATENT DOCUMENTS 3,822,425 A    7/1974  Scales
4,134,166 A *  1/1979  Schuder ........................... 5/710

(Continued)

OTHER PUBLICATIONS

"SensorCell Flotation Therapy Mattress", TheraTorr Medical, Inc., 2010, retrieved Mar. 2, 2011 from http://www.theratorr.com/Technology.html.

(Continued)

*Primary Examiner* — Michael Trettel
*Assistant Examiner* — Myles Throop
(74) *Attorney, Agent, or Firm* — Baker & Hostetler LLP

(57) ABSTRACT

Patient support systems are generally disclosed. An example patient support system may include a base; first and second longitudinally oriented sidewalls extending upward from lateral side portions of the base; a substantially vapor-impermeable barrier on the top surface of the base and on inwardly facing surfaces of the sidewalls; a substantially vapor-permeable top cover extending between the sidewalls such that a generally longitudinally oriented channel configured to receive airflow therethrough is substantially defined by a lower surface of the top cover, an upper surface of the barrier on the base, and inwardly facing surfaces of the barrier on the sidewalls; a supply conduit extending from an exterior air supply connector to an internal air supply opening within the channel; an air discharge opening within the channel; and an inflatable support disposed in the channel. The interior volume of the inflatable support may be fluidicly isolated from the channel.

16 Claims, 17 Drawing Sheets

(56) References Cited

U.S. PATENT DOCUMENTS

| | | | |
|---|---|---|---|
| 4,197,837 A | 4/1980 | Tringali et al. | |
| 4,485,505 A * | 12/1984 | Paul | 5/714 |
| 4,797,962 A | 1/1989 | Goode | |
| 4,946,220 A | 8/1990 | Wyon et al. | |
| 5,755,000 A * | 5/1998 | Thompson | 5/713 |
| 5,887,304 A * | 3/1999 | von der Heyde | 5/726 |
| 6,047,423 A * | 4/2000 | Larson | 5/709 |
| 6,288,076 B1 | 9/2001 | Kostyniak et al. | |
| 6,317,912 B1 | 11/2001 | Graebe et al. | |
| 6,487,739 B1 | 12/2002 | Harker | |
| 6,684,437 B2 | 2/2004 | Koenig | |
| 6,687,936 B2 * | 2/2004 | Graebe et al. | 5/710 |
| 6,687,937 B2 * | 2/2004 | Harker | 5/726 |
| 6,694,556 B2 * | 2/2004 | Stolpmann | 5/710 |
| 6,782,574 B2 * | 8/2004 | Totton et al. | 5/713 |
| 7,165,281 B2 | 1/2007 | Larssson et al. | |
| 7,509,698 B2 | 3/2009 | Poulos | |
| 7,536,739 B2 | 5/2009 | Poulos | |
| 7,587,776 B2 | 9/2009 | Poulos | |
| 7,975,335 B2 * | 7/2011 | O'Keefe et al. | 5/616 |
| 8,108,957 B2 * | 2/2012 | Richards et al. | 5/600 |
| 8,220,090 B2 * | 7/2012 | Gowda | 5/713 |
| 2003/0208849 A1 * | 11/2003 | Wilkinson | 5/713 |
| 2004/0177450 A1 * | 9/2004 | Salvatini et al. | 5/714 |
| 2004/0237203 A1 | 12/2004 | Romano et al. | |
| 2005/0188467 A1 * | 9/2005 | Woolfson | 5/740 |
| 2007/0261548 A1 | 11/2007 | Vrzalik et al. | |
| 2007/0283498 A1 * | 12/2007 | Shelby | 5/706 |
| 2008/0001841 A1 * | 1/2008 | Alberding et al. | 343/872 |
| 2009/0217460 A1 * | 9/2009 | Bobey et al. | 5/709 |
| 2011/0289691 A1 * | 12/2011 | Lafleche et al. | 5/710 |
| 2014/0090176 A1 * | 4/2014 | Boyd | 5/710 |

OTHER PUBLICATIONS

"SensorCell Technology", TheraTorr Medical, Inc., 2010, retrieved Mar. 2, 2011 from http://www.theratorr.com/SensorCell.html.

"TheraTorr Medical, Inc.", TheraTorr Medical, Inc., 2010, retrieved Mar. 2, 2011 from http://www.theratorr.com/.

"The ROHO Dry Flotation Mattress System", The ROHO Group, 2006. [Month of publication is unknown. The year of publication is sufficiently earlier than the effective U.S. filing date and any foreign priority date so the particular month of publication is not an issue.].

"Long Term Care Solutions", American Medical Equipment, Columbus, Ohio. [Month and year of publication is unknown].

"The Total-Lift Bed", VitalGo Systems Ltd., 2008, Williston Park, NY. [Month of publication is unknown. The year of publication is sufficiently earlier than the effective U.S. filing date and any foreign priority date so the particular month of publication is not an issue.].

\* cited by examiner

2000 placing a patient on a substantially vapor-permeable top sheetcover of a support structure, the support structure comprising a generally rectangular base comprising a top surface, a first longitudinally oriented sidewall and a second longitudinally oriented sidewall extending upward from lateral side portions of the base, a substantially vapor-impermeable barrier disposed on the top surface of the base and on inwardly facing surfaces of the first longitudinally oriented sidewall and the second longitudinally oriented sidewall, and an inflatable support, wherein the vapor-permeable top sheetcover extends between upper aspects of the first longitudinally oriented sidewall and the second longitudinally oriented sidewall such that a generally longitudinally oriented channel configured to receive airflow therethrough is substantially defined by a lower surface of the top sheetcover, an upper surface of the barrier on the base, and inwardly facing surfaces of the barrier on the first longitudinally oriented sidewall and the second longitudinally oriented sidewall, wherein the inflatable support is disposed in the channel, and wherein an interior volume of the inflatable support is fluidicly isolated from channel

2002 flowing air through the channel while the patient is on the substantially vapor-permeable top cover

PATIENT SUPPORT SYSTEMS

CROSS-REFERENCE TO RELATED APPLICATIONS

This application claims the benefit of U.S. Provisional Application No. 61/354,214, filed Jun. 12, 2010, which is hereby incorporated by reference.

The subject matter of this application may be related to the subject matter of co-pending U.S. patent application Ser. No. 13/158,725, filed Jun. 13, 2011.

BACKGROUND

The present disclosure generally pertains to patient support systems and, more particularly, to patient support structure systems (sometimes referred to as "support surface" systems) designed to reduce the risk of developing pressure sores and/or to provide patient weighing and/or bed-exit monitoring functions.

SUMMARY

Patient support systems are generally disclosed. Some example embodiments may include methods, apparatus, and/or systems pertaining to patient support structure systems designed to reduce the risk of developing pressure sores and/or to provide patient weighing and/or bed-exit monitoring functions.

Some example patient support systems according to at least some aspects of the present disclosure may include a generally rectangular base comprising a top surface. A first longitudinally oriented sidewall and a second longitudinally oriented sidewall may extend upward from lateral side portions of the base. A substantially vapor-impermeable barrier may be disposed on the top surface of the base and on inwardly facing surfaces of the first longitudinally oriented sidewall and the second longitudinally oriented sidewall. A substantially vapor-permeable top cover may extend between upper aspects of the first longitudinally oriented sidewall and the second longitudinally oriented sidewall such that a generally longitudinally oriented channel configured to receive airflow therethrough may be substantially defined by a lower surface of the top cover, an upper surface of the barrier on the base, and inwardly facing surfaces of the barrier on the first longitudinally oriented sidewall and the second longitudinally oriented sidewall. A supply conduit may extend from an exterior air supply connector to an internal air supply opening within the channel. An air discharge opening within the channel may be arranged to allow air to exit the channel. An inflatable support may be disposed in the channel. An interior volume of the inflatable support may be fluidically isolated from the channel.

Some example methods of operating a patient support system according to at least some aspects of the present disclosure may include placing a patient on a substantially vapor-permeable top cover of a support structure. The support structure may include a generally rectangular base including a top surface. A first longitudinally oriented sidewall and a second longitudinally oriented sidewall may extend upward from lateral side portions of the base. A substantially vapor-impermeable barrier may be disposed on the top surface of the base and on inwardly facing surfaces of the first longitudinally oriented sidewall and the second longitudinally oriented sidewall, and an inflatable support. The vapor-permeable top cover may extend between upper aspects of the first longitudinally oriented sidewall and the second longitudinally oriented sidewall such that a generally longitudinally oriented channel configured to receive airflow therethrough may be substantially defined by a lower surface of the top cover, an upper surface of the barrier on the base, and inwardly facing surfaces of the barrier on the first longitudinally oriented sidewall and the second longitudinally oriented sidewall. The inflatable support may be disposed in the channel. An interior volume of the inflatable support may be fluidically isolated from channel. A method may include flowing air through the channel while the patient is on the substantially vapor-permeable top cover.

Some example methods of providing a predictive bed-exit alarm according to at least some aspects of the present disclosure may include receiving a patient on a support structure. The support structure may include a plurality of fluidicly independent inflatable supports disposed within the support structure and inflated to respective unloaded pressures. Each of the plurality of inflatable supports may be configured to support at least a portion of the patient's weight when the patient is in a generally supine position on the support structure. A method may include monitoring a respective loaded pressure of each of the plurality of inflatable supports. The loaded pressure of each of the plurality of inflatable supports may be above the respective unloaded pressure. A method may include initiating a predictive bed-exit alarm sequence upon determining that the pressure of at least one of the plurality of inflatable supports is at about its unloaded pressure.

Some example support structure systems according to at least some aspects of the present disclosure may include a support structure configured to receive a patient. The support structure may include a first inflatable support and a second inflatable support disposed within the support structure. The first inflatable support and the second inflatable support may be independently inflatable. Each of the first inflatable support and the second inflatable support may support at least a portion of the patient's weight when the patient is in a generally supine position on the support structure. The first inflatable support and the second inflatable support may have respective unloaded pressures. The first inflatable support and the second inflatable support may have respective loaded pressures when the patient is in the generally supine position on the support structure. The respective loaded pressures may be greater than the respective unloaded pressures. A support structure system may include an alarm system, which may include a first pressure detector associated with the first inflatable support; a second pressure detector associated with the second inflatable support; and an alarm logic configured to receive data associated with a detected pressure of the first inflatable support, to receive data associated with a detected pressure of the second inflatable support, and to initiate a predictive bed-exit alarm sequence upon determining that at least one of the detected pressure of the first inflatable support and the detected pressure of the second inflatable support is at about its respective unloaded pressure.

Some example patient weighing systems according to at least some aspects of the present disclosure may include an inflatable mat configured to be disposed on a bed frame and beneath a support structure. The inflatable mat may include an upper, substantially air-impermeable layer; a lower, substantially air-impermeable layer; and a middle volume interposing the upper layer and the lower layer. The middle volume may include a plurality of threads connecting the upper layer and the lower layer at a substantially fixed distance. The upper layer and the lower layer may form a substantially air-tight volume housing the middle volume. The patient weighing system may include a pressure sensor arranged to sense an inflation pressure of the inflatable mat and a user interface unit operatively connected to the pressure sensor. The interface unit may be programmed to detect a difference between an unloaded pressure of the mat and a loaded pressure of the mat and to output a patient weight corresponding to the difference.

Some example methods of determining a patient weight according to at least some aspects of the present disclosure may include receiving a patient on a support structure. The support structure may be supported by an inflatable mat. The inflatable mat may include an upper, substantially air-impermeable layer, a lower, substantially air-impermeable layer, and a middle volume interposing the upper layer and the lower layer. The middle volume may include a plurality of threads connecting the upper layer and the lower layer at a substantially fixed distance. The method may include sensing a loaded pressure of the inflatable mat and outputting a patient weight corresponding to a difference between the loaded pressure of the inflatable mat and an unloaded pressure of the inflatable mat.

Some example patient support systems according to at least some aspects of the present disclosure may include a support structure configured to receive a patient. The support structure may include a first inflatable support and a second inflatable support. The first inflatable support and the second inflatable support may be independently inflatable. Each of the first inflatable support and the second inflatable support may support at least a portion of the patient's weight when the patient is in a generally supine position on the support structure. The first inflatable support and the second inflatable support may have respective unloaded pressures. The first inflatable support and the second inflatable support may have respective loaded pressures when the patient is in the generally supine position on the support structure. The respective loaded pressures being greater than the respective unloaded pressures. A patient support system may include an inflatable mat disposed between the first and second inflatable supports and a bed frame. The inflatable mat may include an upper, substantially air-impermeable layer, a lower, substantially air-impermeable layer, and a middle volume interposing the upper layer and the lower layer. The middle volume may include a plurality of threads connecting the upper layer and the lower layer at a substantially fixed distance. The upper layer and the lower layer may form a substantially air-tight volume housing the middle volume. A patient support system may include a first pressure detector associated with the first inflatable support, a second pressure detector associated with the second inflatable support, an inflatable mat pressure sensor arranged to sense an inflation pressure of the inflatable mat, and a user interface unit. The user interface unit may include an alarm logic configured to receive data associated with a detected pressure of the first inflatable support, to receive data associated with a detected pressure of the second inflatable support, and to initiate a predictive bed-exit alarm sequence upon determining that at least one of the detected pressure of the first inflatable support and the detected pressure of the second inflatable support is at about its respective unloaded pressure. A user interface unit may include a patient weight display configured to indicate a patient weight calculated by a patient weight logic. The patient weight logic may be operatively connected to the inflatable mat pressure sensor. The patient weight logic may be programmed to detect a difference between an unloaded pressure of the inflatable mat and a loaded pressure of the inflatable mat and to output the patient weight based at least partially on the difference.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 14 is a flowchart of an example method of operating a patient support system;

DETAILED DESCRIPTION

Figure 1:
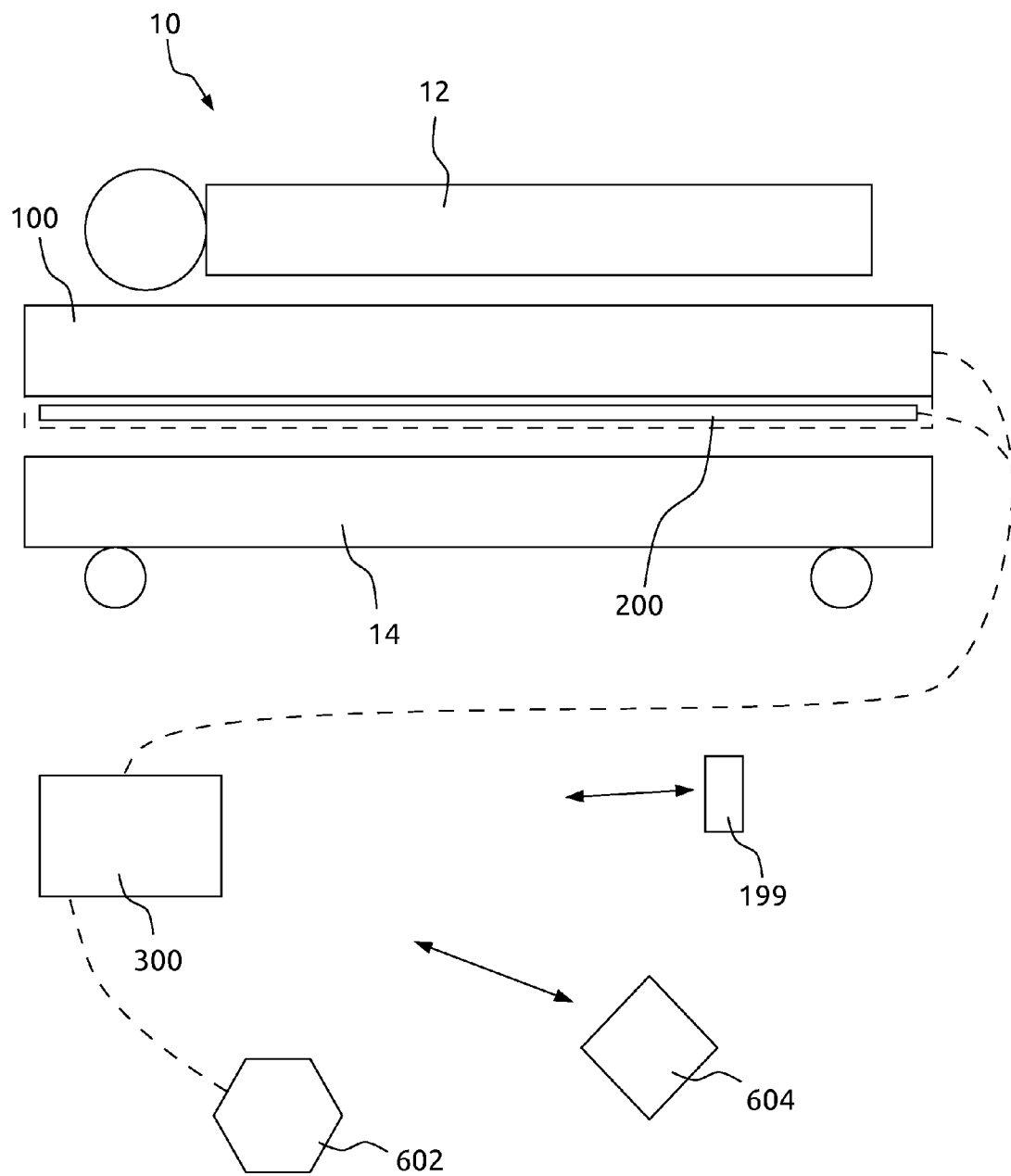
FIG. 1 is a block diagram of an example patient support system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

Methods, systems, devices, and/or apparatus related to patient support systems are described. Some example embodiments according to the present disclosure may pertain to patient support structure systems designed to reduce the risk of developing pressure sores and/or to provide patient weighing and/or bed-exit monitoring functions.

FIG. 1 is a block diagram of an example patient support system 10, according to at least some embodiments of the present disclosure. A patient may lie on a support structure 100 (which may be referred to as a mattress), which may be disposed on a bed frame 14, such as a hospital bed frame. In some example embodiments, a mat 200 may interpose mattress 100 and bed frame 14. In some example embodiments, support structure 100 and/or mat 200 may be operatively connectable to a control unit 300.

Control unit 300, support structure 100, and/or sensor mat 200 may be configured to perform functions such as, for example and without limitation, supplying air to and/or venting air from one or more inflatable portions of support structure 100, flowing air through one or more portions of support structure 100, and/or sensing, displaying, and/or recording various parameters and/or events associated with support structure 100 and/or mat 200. In some example embodiments, control unit 300 may be operatively connectable to an external power source 602 and/or an external communication device 604 (e.g., via a wired and/or wireless connection). In some example embodiments, a remote control 199 may be operatively connected to control unit 300, such as by a wired and/or wireless connection.

Figure 2:
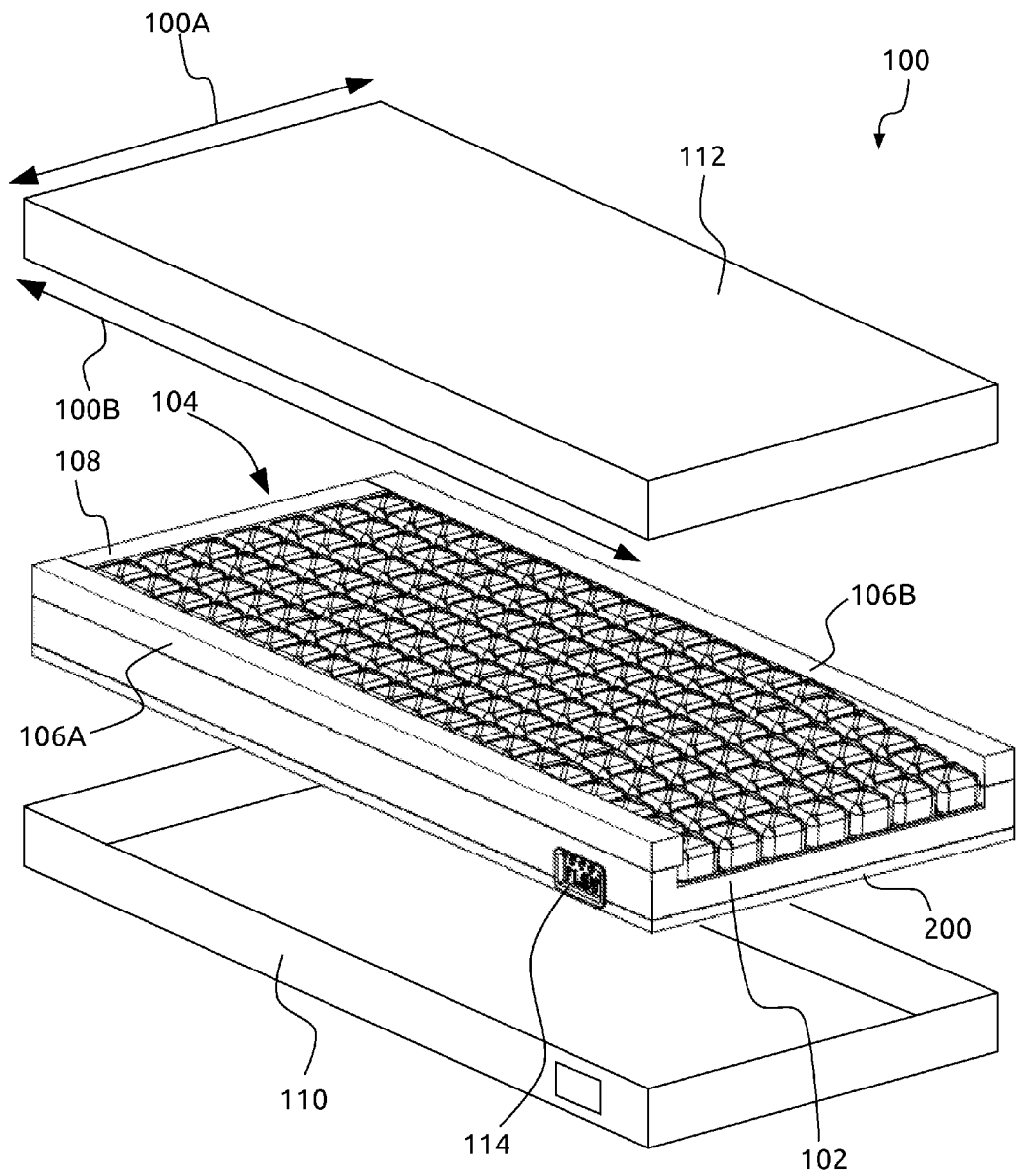
FIG. 2 is an exploded perspective view of an example support structure.

FIG. 2 is an exploded perspective view of an example support structure 100, according to at least some embodiments of the present disclosure. Support structure 100 may include a base 102, one or more inflatable supports 104 (which may be disposed substantially within support structure 100), one or more longitudinally oriented side walls 106A, 106B extending upward from lateral side portions of base 102, one or more end walls (e.g., a head end wall 108, which may extend upward from a head end portion of base and/or may extend laterally from side wall 106A to side wall 106B), a bottom cover 110, and/or a top cover 112. Base 102 may be generally rectangular and/or may extend for substantially the entire width 100A of mattress 100 and/or substantially the entire length 100B of mattress 100.

In some example embodiments, mat 200 may be disposed within bottom cover 110 beneath base 102, and in some example embodiments mat 200 may be disposed beneath bottom cover 110 (e.g., between bottom cover 110 and bed frame 14 (FIG. 1)). Inflatable support 104 may have a width less than width 100A of support structure 100 and/or a length less than length 100B of mattress 100. Some example embodiments may not include both side walls 106A, 106B and/or head end wall 108, and some example embodiments may additionally include a foot end wall generally similar to head end wall 108. Some example embodiments may include an external connection panel 114, which may include one or more connectors coupled to internal components of support structure 100 as described below.

Figure 3:
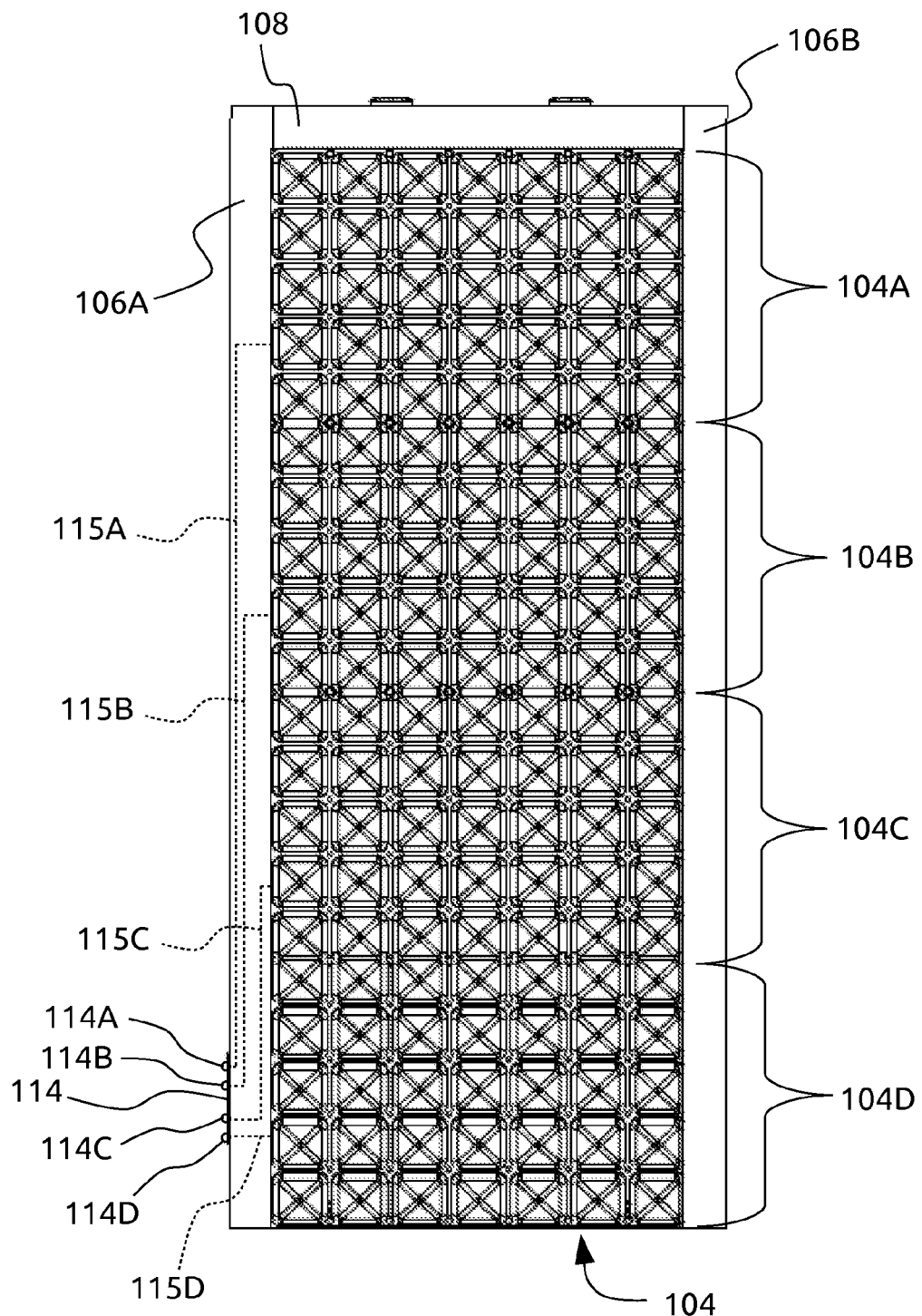
FIG. 3 is a plan view of an example support structure with the top cover removed.

FIG. 3 is a plan view of an example support structure 100 with top cover 112 removed, according to at least some embodiments of the present disclosure. In some example embodiments, inflatable support 104 may include one or more sections, each of which may comprise a plurality of fluidicly connected, upstanding chambers. For example, in some example embodiments, inflatable support 104 may include inflatable support sections 104A, 104B, 104C, 104D arranged from head to foot (e.g., a head section, a torso section, a hip section, and a foot section).

Individual support sections 104A, 104B, 104C, 104D may comprise about 35 fluidicly connected, upstanding chambers. For example, individual support sections 104A, 104B, 104C, 104D may be generally similar to those manufactured by ROHO Group, Inc. of Belleville, Ill. In some example embodiments, individual chambers may be about 3" wide by about 3" long by about 2½" high and/or may be constructed at least partially from urethane. In some example embodiments, individual chambers may be about 1" wide by about 1" long by about 3" high and/or may be constructed at least partially from neoprene.

In some example embodiments, inflatable support sections 104A, 104B, 104C, 104D may be individually inflated or deflated as desired. For example, inflatable support sections 104A, 104B, 104C, 104D may be inflated to respective unloaded pressures prior to the patient being received on support structure 100. Respective loaded pressures (e.g., when a patient is lying on support structure 100) of inflatable support sections 104A, 104B, 104C, 104D may be greater than the respective unloaded pressures.

In some example embodiments, external connection panel 114 may comprise one or more connectors 114A, 114B, 114C, 114D, which may be fluidicly connected to inflatable support sections 104A, 104B, 104C, 104D via channels 115A, 115B, 115C, 115D (such as may be provided by tubing or a manifold), respectively. One or more of connectors 114A, 114B, 114C, 114D may comprise quick-disconnect fittings, which may be internally valved to prevent leakage of air from inflatable support sections 104A, 104B, 104C, 104D when disconnected. Connectors 114A, 114B, 114C, 114D may be operatively coupled to control unit 300, which, for example, may sense respective pressures of inflatable support sections 104A, 104B, 104C, 104D and/or may provide air to or vent air from of inflatable support sections 104A, 104B, 104C, 104D.

Figure 4A:
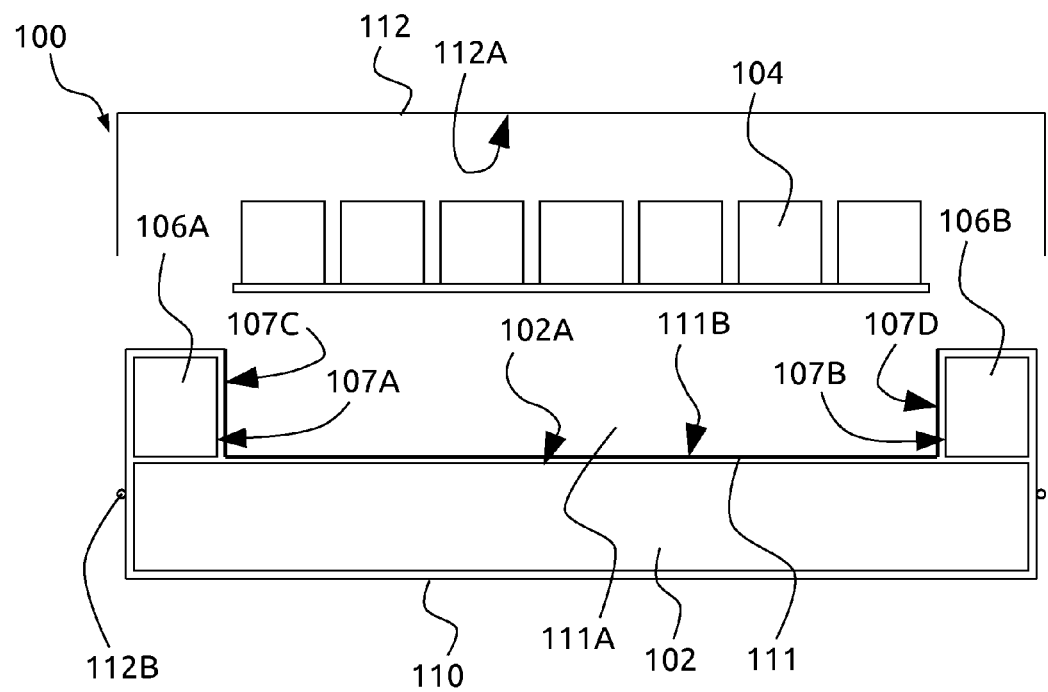
FIG. 4A is an exploded cross-sectional view of an example support structure.
Figure 4B:
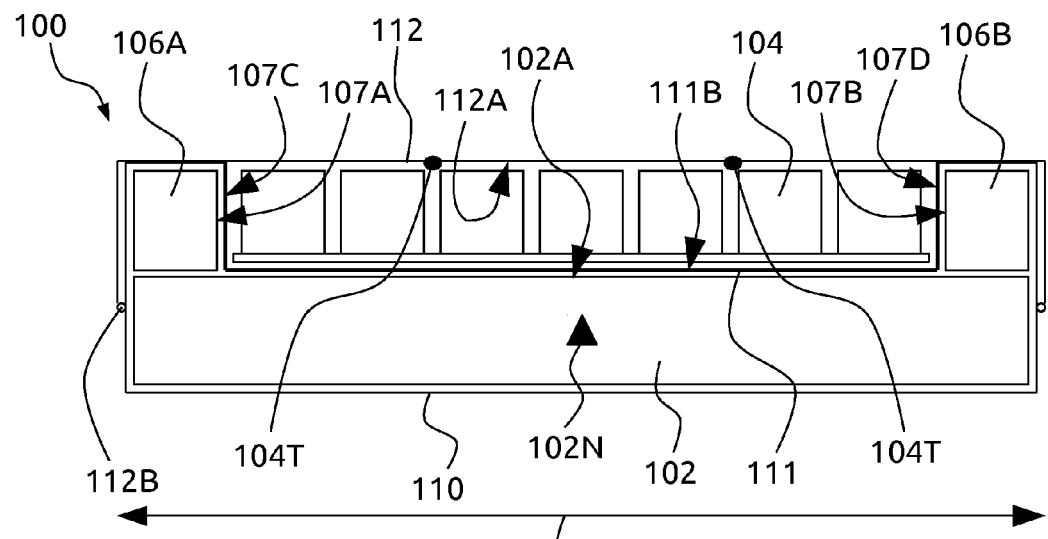
FIG. 4B is a cross-sectional view of an example support structure.

FIGS. 4A and 4B are an exploded cross-sectional view of an example support structure 100 and a cross-sectional view of an example support structure 100, respectively, according to at least some embodiments of the present disclosure. Base 102 may include a top surface 102A, which may be substantially planar. Inflatable support 104, side walls 106A, 106B, and/or head end wall 108 (see FIG. 2) may be positioned on top surface 102A of base 102 and/or may be at least partially enclosed by fabric or other covering, which may comprise portions of bottom cover 110. In an assembled support structure 100, inflatable support 104 may lie within a cavity at least partially defined below by top surface 102A of base 102, on the lateral sides by inwardly facing surfaces 107A, 107B of side walls 106A, 106B, and/or on the head end by head end wall 108.

In some example embodiments, a substantially vapor-impermeable barrier 111 may be disposed on at least a portion of top surface 102A of base 102 and/or on inwardly facing surfaces 107A, 107B of side walls 106A, 106B. In some example embodiments, barrier 111 may comprise a portion of bottom cover 110. In some example embodiments, top cover 112 may be releasably joined to bottom cover 110 by a fastener, such as zipper 112B.

In some example embodiments, an upper surface 111B of barrier 111 on base 102, inwardly facing surfaces 107C, 107D of barrier 111 on side walls 106A, 106B, and/or at least a portion of a lower surface 112A of top cover 112 may substantially define a generally longitudinally oriented channel 111A. Inflatable support 104 may be disposed within channel 111A and/or an interior volume of inflatable support 104 may be fluidicly isolated from channel 111A.

In some example embodiments, support structure 100 may include one or more sensors, which may be operatively coupled control unit 300. Example sensors may include one or more temperature sensors 104T (e.g., an infrared temperature sensor), one or more humidity sensors 104H, and/or one or more angle sensors 102N (e.g., a potentiometer). Temperature sensor 104T and/or humidity sensor 104H may be configured to detect conditions approximate top cover 112, which may be indicative of conditions at an interface between a patient and support structure 100. Angle sensor 102N may be configured to detect the angle of elevation of the head portion of support structure 100 and/or may be mounted within and/or on base 102.

In some example embodiments, base 102, side walls 106A, 106B, and/or head end wall 108 may be constructed from foam (e.g., polyurethane foam) and/or non-foam materials. Example non-foam materials include, but are not limited to, fibrous materials (e.g., non-woven, randomly oriented polyester fiber materials, such as Indura Performance Fiber, available from Indratech of Auburn Hills, Mich.), gels, viscous fluids such as silicone, and/or other natural or manmade materials conventionally utilized in mattresses and/or tubes. In some example embodiments, base 102, side walls 106A, 106B, and/or head end wall 108 may comprise one or more air bladders. For example, in some example embodiments, base 102 may be constructed from foam and/or side walls 106A, 106B may be constructed from a non-foam material. In other example embodiments, base 102 may comprise one or more air bladders, without foam. In other example embodiments, side walls 106A, 106B may comprise one or more air bladders.

Figure 5:
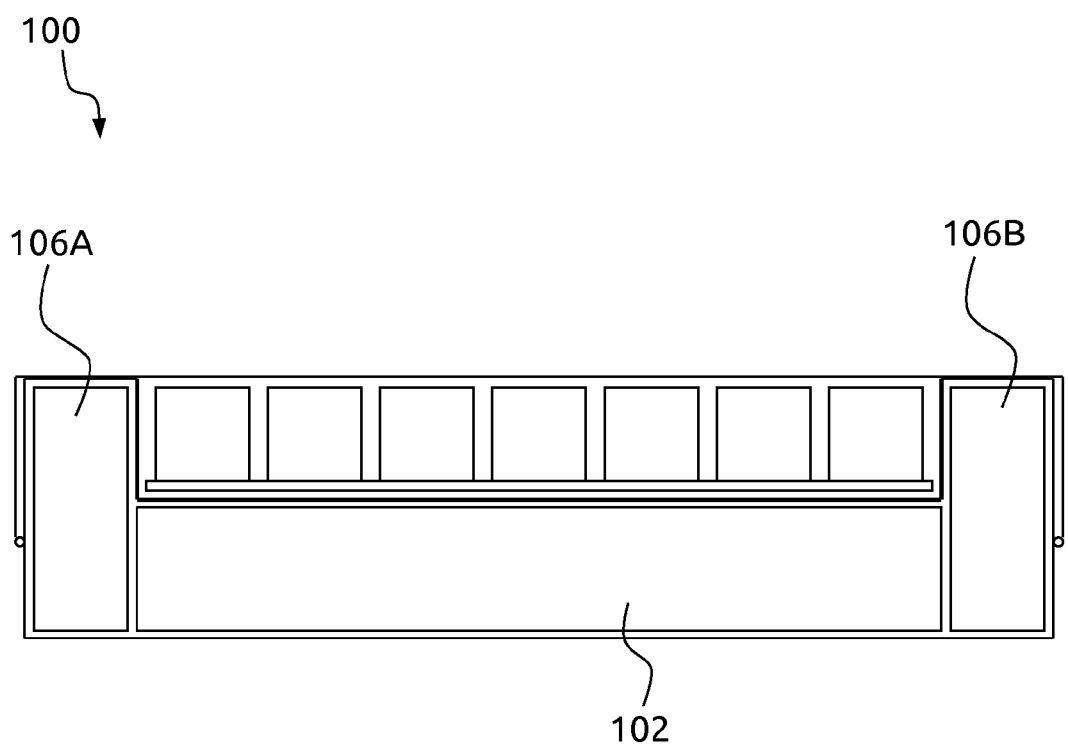
FIG. 5 is a cross-sectional view of an example support structure illustrating an alternative arrangement of the side walls.

FIG. 5 is a cross-sectional view of an example support structure illustrating an alternative arrangement of side walls 106A, 106B, according to at least some embodiments of the present disclosure. In some example embodiments, side walls 106A, 106B may be disposed against outwardly facing lateral side edges of base 102.

Figure 6:
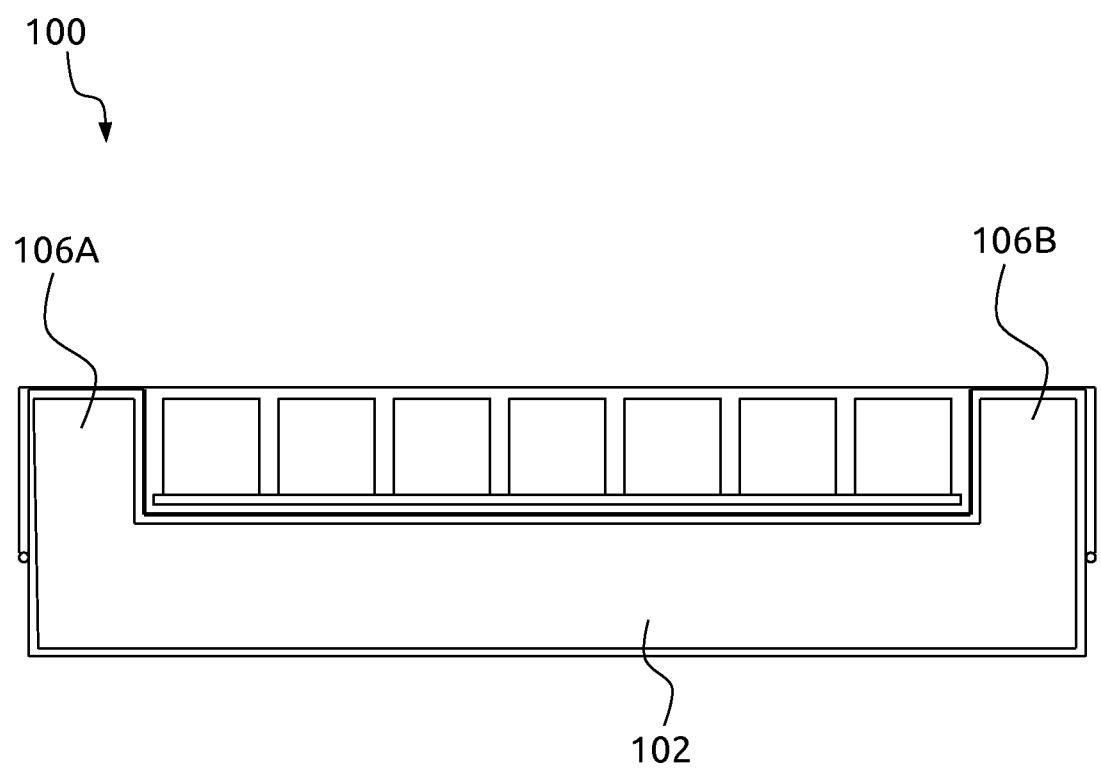
FIG. 6 is a cross-sectional view of an example support structure illustrating the side walls integrally formed with the base.

FIG. 6 is a cross-sectional view of an example support structure illustrating side walls 106A, 106B integrally formed with base 102, according to at least some embodiments of the present disclosure. In some example embodiments, side walls 106A, 106B may be integrally formed with base 102.

Figure 7:
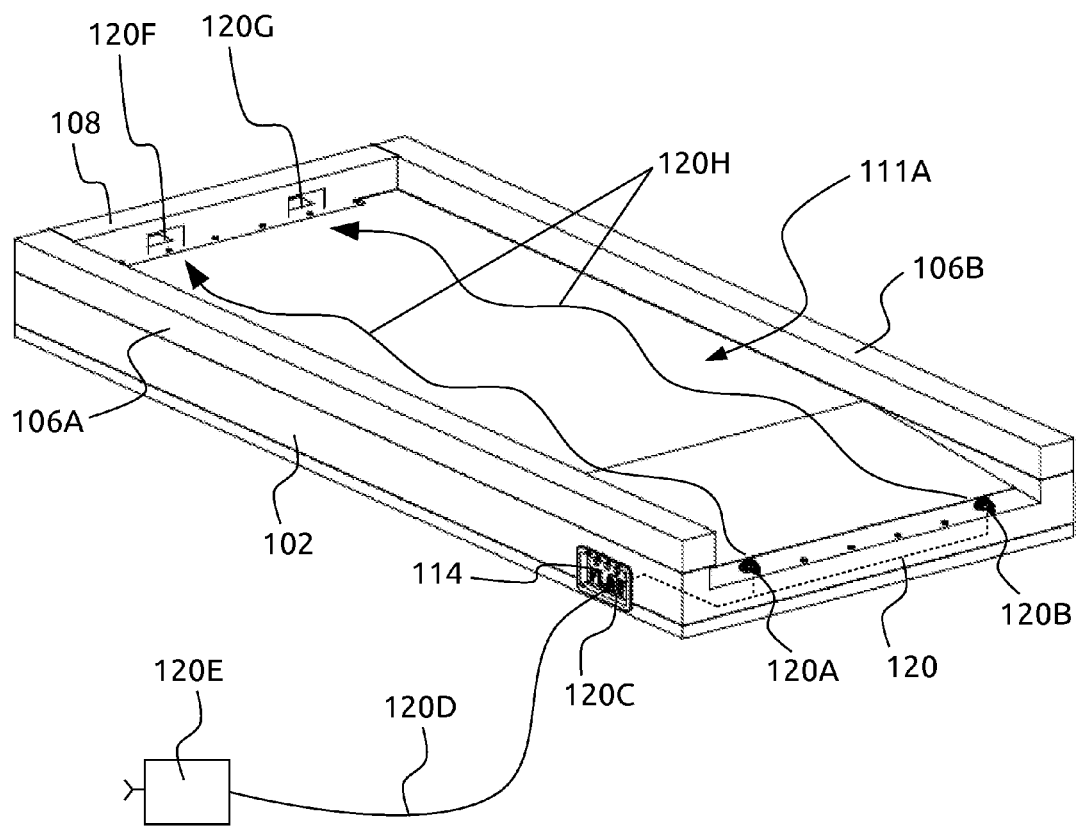
FIG. 7 is a perspective view of an example base, side walls, and head end wall.

FIG. 7 is a perspective view of an example base 102, side walls 106A, 106B, and head end wall 108, according to at least some embodiments of the present disclosure. Some example embodiments may be configured to provide forced air flow through support structure 100, which may be referred to as "low air loss." For example, as illustrated in FIG. 7, some embodiments may include an internal air supply conduit 120 extending from an exterior air supply connector 120C (which may be disposed on external connection panel 114) to one or more internal air supply openings 120A, 120B.

In some example embodiments, internal air supply openings 120A, 120B may be disposed within channel 111A approximate a foot end of base 102. Air may be supplied to exterior air supply connector 120C from an air source 120E (e.g., a blower) via an external air supply conduit 120D. In some example embodiments, air source 120E may be provided as part of or in connection with to control unit 300 (FIG. 1).

Some example embodiments may include one or more air discharge openings 120F, 120G, which may be arranged to allow air to exit channel 111A, such as to an ambient environment. Air discharge openings 120F, 120G may extend through head end wall 108, for example, and may be disposed within channel 111A approximate the head end of base 102. Delivering air to channel 111A via internal air supply openings 120A, 120B and venting air through air discharge openings 120F, 120G may cause air flow along generally foot-to-head flowpaths 120H.

Some example embodiments may be configured so that air flow through support structure 100 (e.g., low air loss air flow) may be substantially independent of the air within the interiors of inflatable support sections 104A, 104B, 104C, 104D. Accordingly, a patient receiving low air loss therapy may remain supported by inflatable support sections 104A, 104B, 104C, 104D, even if air source 120E is turned off, unplugged, etc. Similarly, support structure 100 may be used without low air loss therapy, if desired. In some example embodiments, the independence of the inflation of inflatable support sections 104A, 104B, 104C, 104D and the low air loss air flow may allow use of a smaller, quieter, and more energy efficient air source 120E than may be required for conventional low air loss systems in which the air source may provide both supporting inflation and air flow.

Figure 8:
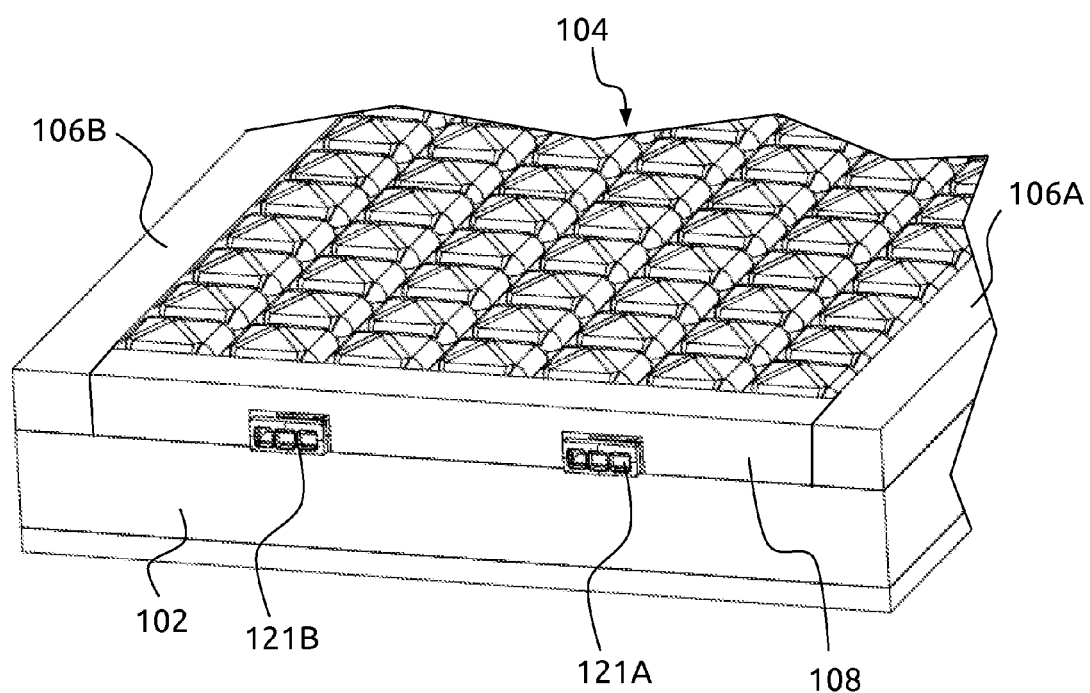
FIG. 8 is a detailed perspective view of a head end of an example support structure.

FIG. 8 is a detailed perspective view of a head end of an example support structure 100, according to at least some embodiments of the present disclosure. Some example embodiments may include grates 121A, 121B, which may provide vent paths from air discharge openings 120F, 120G (FIG. 7) through head end wall 108 and/or top cover (FIG. 2). Grates 121A, 121B may house one or more filters, which may comprise mesh screens. Example mesh screens may include a sintered stainless steel mesh (e.g., about 44 micron).

Figure 9:
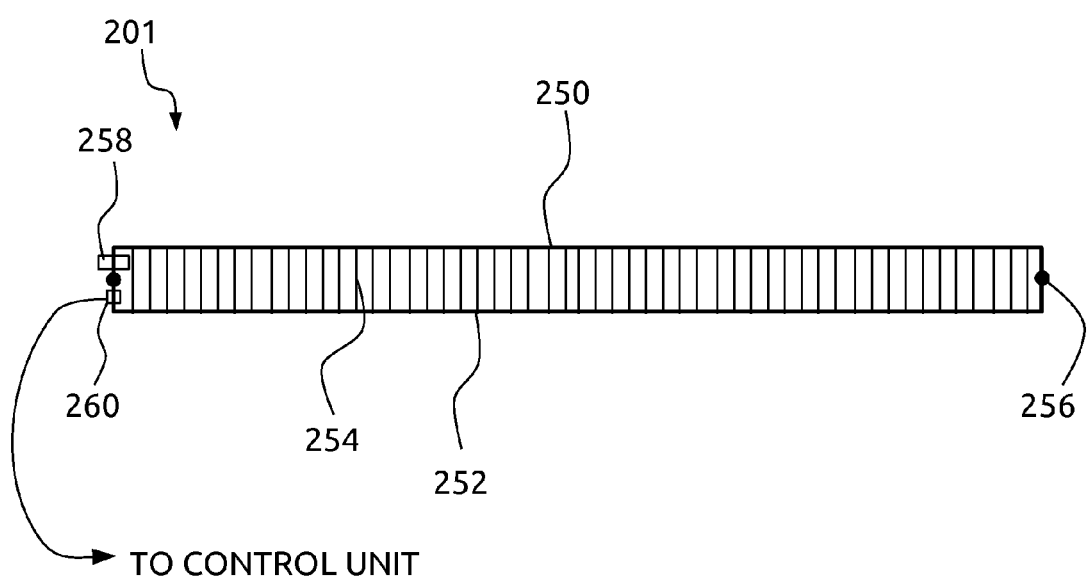
FIG. 9 is a cross-sectional view of an example inflatable mat.

FIG. 9 is a cross-section view of an example inflatable mat 201, according to at least some embodiments of the present disclosure. Inflatable mat 201 may comprise mat 200, described above. Inflatable mat 201 may be configured to be disposed on bed frame 14 (FIG. 1) and beneath support structure 100, such as within the outer covering (e.g., bottom cover 110) of support structure 100 and beneath the patient support components (e.g., base 102 and inflatable supports 104). Alternatively, inflatable mat 201 may be disposed between the outer covering (e.g., bottom cover 110) of support structure 100 and bed frame 14. Some example inflatable mats 201 may be sized to underlie substantially the entire base 102 and/or the entire support structure 100.

Some example inflatable mats 201 may comprise a drop-stitch fabric, which may comprise an upper, substantially air-impermeable layer 250; a lower, substantially air-impermeable layer 252; and/or a middle volume 254, which may interpose upper layer 250 and lower layer 252. Middle volume 254 may comprise a plurality of threads connecting upper layer 250 and lower layer 252 at a substantially fixed distance. Upper layer 250 and lower layer 252 may be sealed together (e.g., at seal 256) to provide a substantially air-tight volume housing middle volume 254. Some example embodiments may include an inflation port 258 and/or a pressure sensor 260, which may be configured to sense an inflation pressure of inflatable mat 201 and/or may be operatively coupled to control unit 300. In some example embodiments, inflatable mat 201 may be about 1 inch thick.

In some example embodiments, inflatable mat 201 may be inflated to an unloaded pressure prior to the patient being received on support structure 100. A loaded pressure (when the patient is lying on support structure 100) of inflatable mat 201 may be greater than the unloaded pressure.

Figure 10:
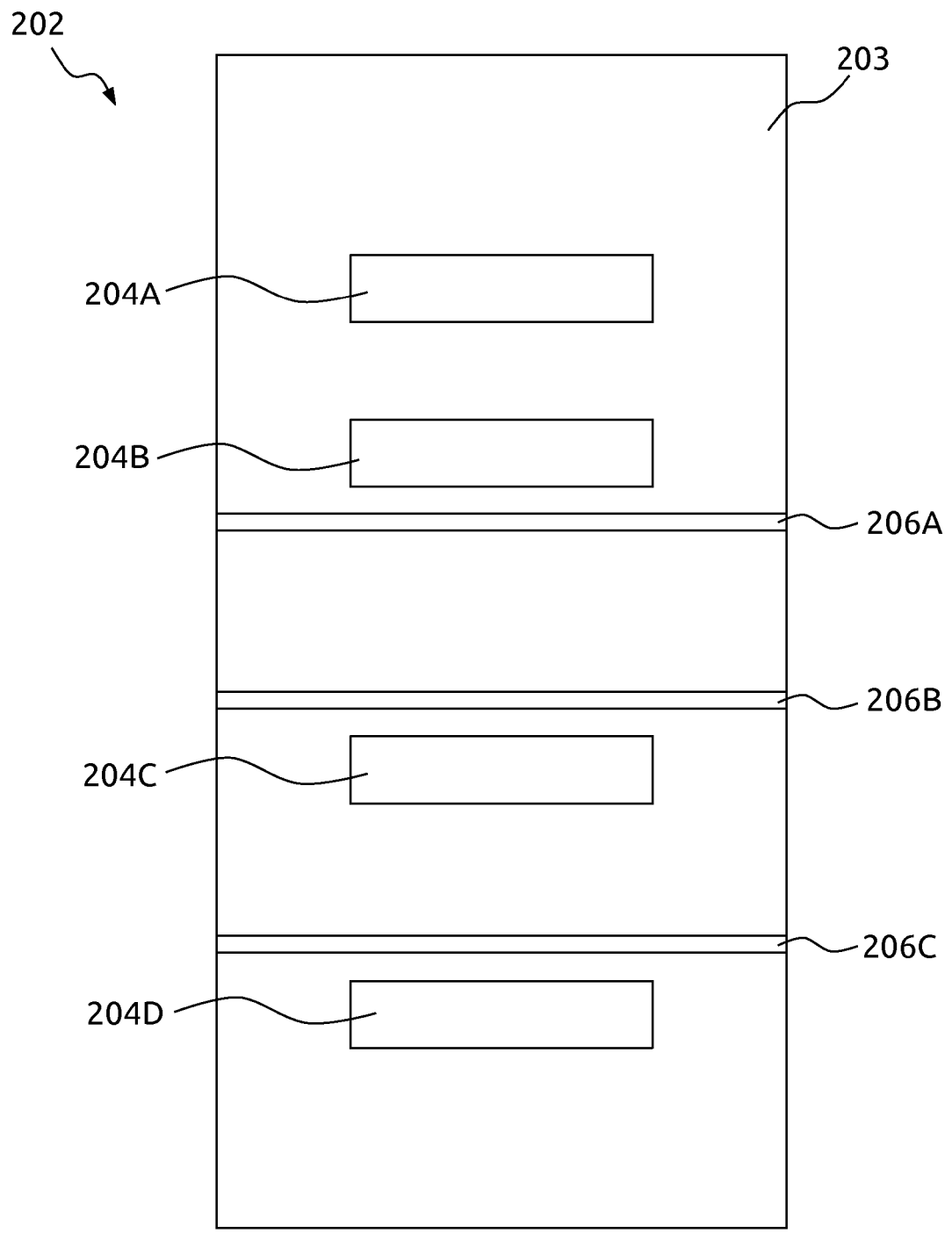
FIG. 10 is a plan view of an example proximity sensor mat.

FIG. 10 is a plan view of an example proximity sensor mat 202, according to at least some embodiments of the present disclosure. Proximity sensor mat 202 may include a pad 203 to which one or more proximity sensor pads 204A, 204B, 204C, 204D may be mounted. One or more slots 206A, 206B, 206C may be provided in pad 203 to allow pad 203 to flex with support structure 100 and/or base 102 as bed frame 14 is articulated, such as to raise and/or lower a patient's head and/or feet. In some example embodiments, proximity sensor mat 202 may be about 1 inch thick.

In some example embodiments, proximity sensor pads 204A, 204B, 204C, 204D may be configured to detect the depth of immersion of a patient in support structure 100. In some example embodiments, an individual proximity sensor pad 204A, 204B, 204C, 204D may comprise a copper-clad printed circuit board configured to act as an antenna. When an object with sufficient mass/dielectric constant (e.g., the patient's body or similar sized object) enters the field of detection, a capacitive sensor may open or close a switch to provide a detection signal. In some example embodiments, the sensitivity of proximity sensor pads 204A, 204B, 204C, 204D may be adjusted such that the signal is provided when the patient is detected at a predetermined depth of immersion, which may be, for example, a maximum desired depth of immersion. In some example embodiments, proximity sensor pads 204A, 204B, 204C, 204D may be wired together in a manner designed minimize interference with one another, such as in a master-slave configuration. Such a configuration may minimize interference caused due to field overlap, such as when bed frame 14 is articulated. In some example embodiments, proximity sensor pads 204A, 204B, 204C, 204D may be about 4 inches by about 16 inches.

In some example embodiments, support structure 100 may include proximity sensor mat 202 integrally constructed therewith. For example, sensor mat 200 may be provided between base 102 and bottom cover 110, beneath base 102. In some example embodiments, sensor mat may be provided separately from support structure 100 and may be placed between bottom cover 110 of support structure 100 and bed frame 14, beneath bottom cover 110.

Some example sensor mats 202 may be operated as follows. Proximity sensor pads 204A, 204B, 204C, 204D may utilize capacitance to detect the presence of the patient on support structure 100. In general, capacitive sensors may utilize a capacitive source to reflect a signal and, in these circumstances, the only significant reflection may be due to the patient on support structure 100. Other materials within support structure 100 may not substantially reflect a signal. Proximity sensor pads 204A, 204B, 204C, 204D may be configured to provide an electrical signal when the patient is detected within a pre-determined distance. This distance may correspond to the depth of immersion of the patient into inflatable support 104. Proximity sensor pads 204A, 204B, 204C, 204D may also be utilized to detect whenever the patient moves beyond a certain distance, thereby supporting a bed exit alarm function.

Some example depth of immersion control functions may be implemented as follows. A minimum desired depth of immersion may be established as a setpoint for proximity sensor pads 204A, 204B, 204C, 204D. If the any of proximity sensor pads 204A, 204B, 204C, 204D detects the patient lower than the set point, it may provide an electrical signal indicating that it has detected the patient below the set point depth. In some example embodiments, an inflation system (described below) of control unit 300 may respond to the detection by further inflating the inflatable support section 104A, 104B, 104C, 104D corresponding to the proximity sensor pad 204A, 204B, 204C, 204D which detected the patient below the setpoint depth. Once the desired inflation has been achieved, inflation may be stopped. Similarly, control unit 300 may direct deflation of an inflatable support section 104A, 104B, 104C, 104D where the patient is detected at less than a desired depth of immersion.

Example control units 300 according to at least some aspects of the present disclosure may comprise various systems and/or may be configured to perform various functions, depending on the desired characteristics of the particular embodiments. Accordingly, the following description pertains to various optional systems, components, and/or functions, and example control units 300 may comprise any number of these and other systems, components, and/or functions.

Figure 11:
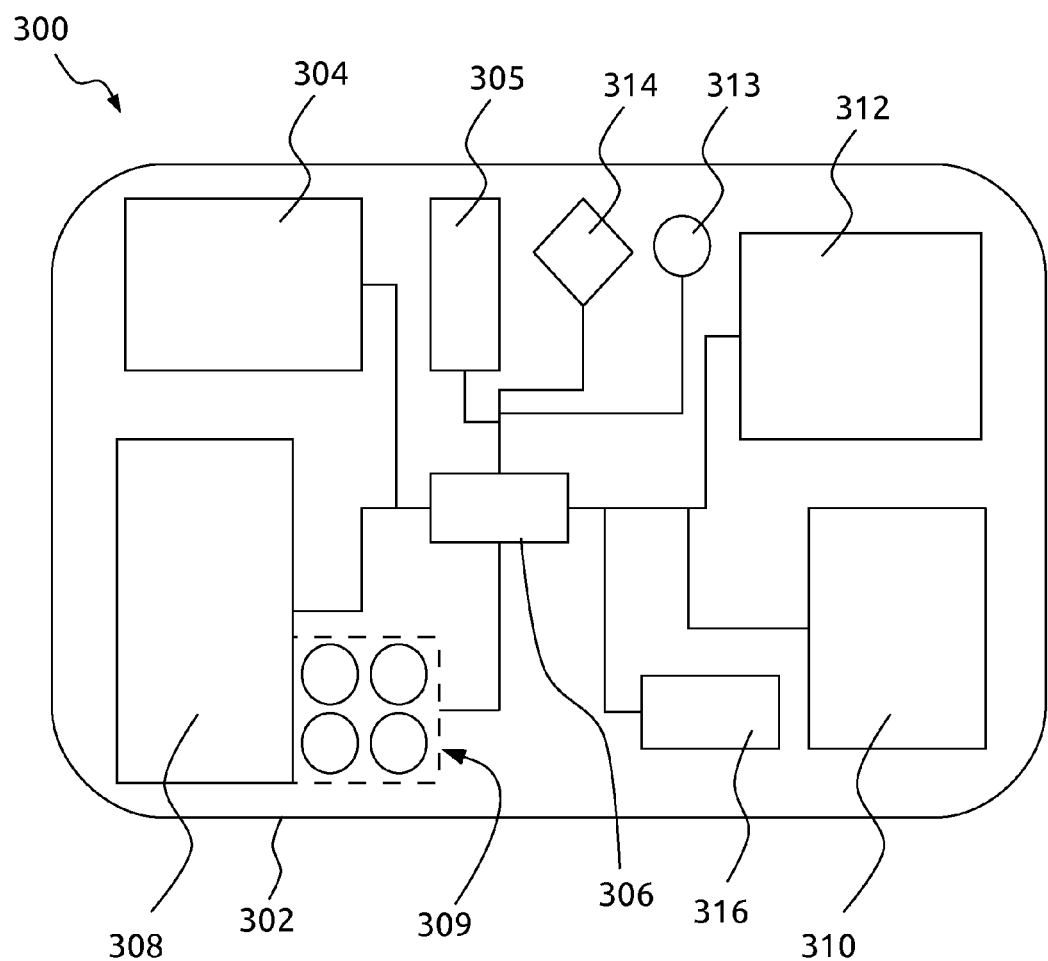
FIG. 11 is a block diagram of an example control unit.

FIG. 11 is a block diagram of an example control unit 300, according to at least some embodiments of the present disclosure. Control unit 300 may include a housing 302, a display 304 (e.g., a touch screen, a liquid crystal display (LCD), light, etc.), a user interface 305 (e.g., a touch screen, button, switch, etc.), a processor 306 (e.g., a computer system, microprocessor, etc., and appropriate associated circuitry), an inflation system 308, inflatable support pressure sensors 309, an ancillary medical device 310, a low air loss air source 312 (e.g., a 50 liter per minute pump/blower), a microphone 313, an alert device 314 (e.g., a buzzer, a speaker, a bell, a light, etc.), and/or a memory 316. In some example embodiments, inflatable support pressure sensors 309 may be disposed in housing 302 and may be fluidicly coupled to respective inflatable support sections 104A, 104B, 104C, 104D. In some example embodiments, inflatable support pressure sensors 309 may be disposed within support structure 100, such as approximate respective inflatable support sections 104A, 104B, 104C, 104D, and may be electrically coupled to processor 306 of control unit 300. Inflatable support pressure sensors 309 may be provided as components of inflation system 308 or separately.

Processor 306 may be operatively connected to display 304, user interface 305, inflation system 308, inflatable support pressure sensors 309, ancillary medical device, low air loss air source 312, microphone 313, alert device 314, memory 316, inflatable mat 201 (e.g., pressure sensor 260), proximity sensor mat 202 (e.g., sensor pads 204A, 204B, 204C, 204D), temperature sensor 104T, humidity sensor 104H, angle sensor 102N, and/or other sensors (e.g., an external moisture/incontinence sensor provided in a sheet and/or patient clothing), for example. Control unit 300 and its various components may be powered from an external power source (e.g., a wall plug) and/or may include a battery for temporary or normal use. Some example embodiments may be configured to transmit and/or receive data as discussed in detail below.

Example ancillary medical devices include, without limitation, deep vein thrombosis treatment devices (which may provide intermittent compression of stockings) and negative pressure wound therapy devices (which may apply a vacuum to a dressing placed over a wound).

Figure 12:
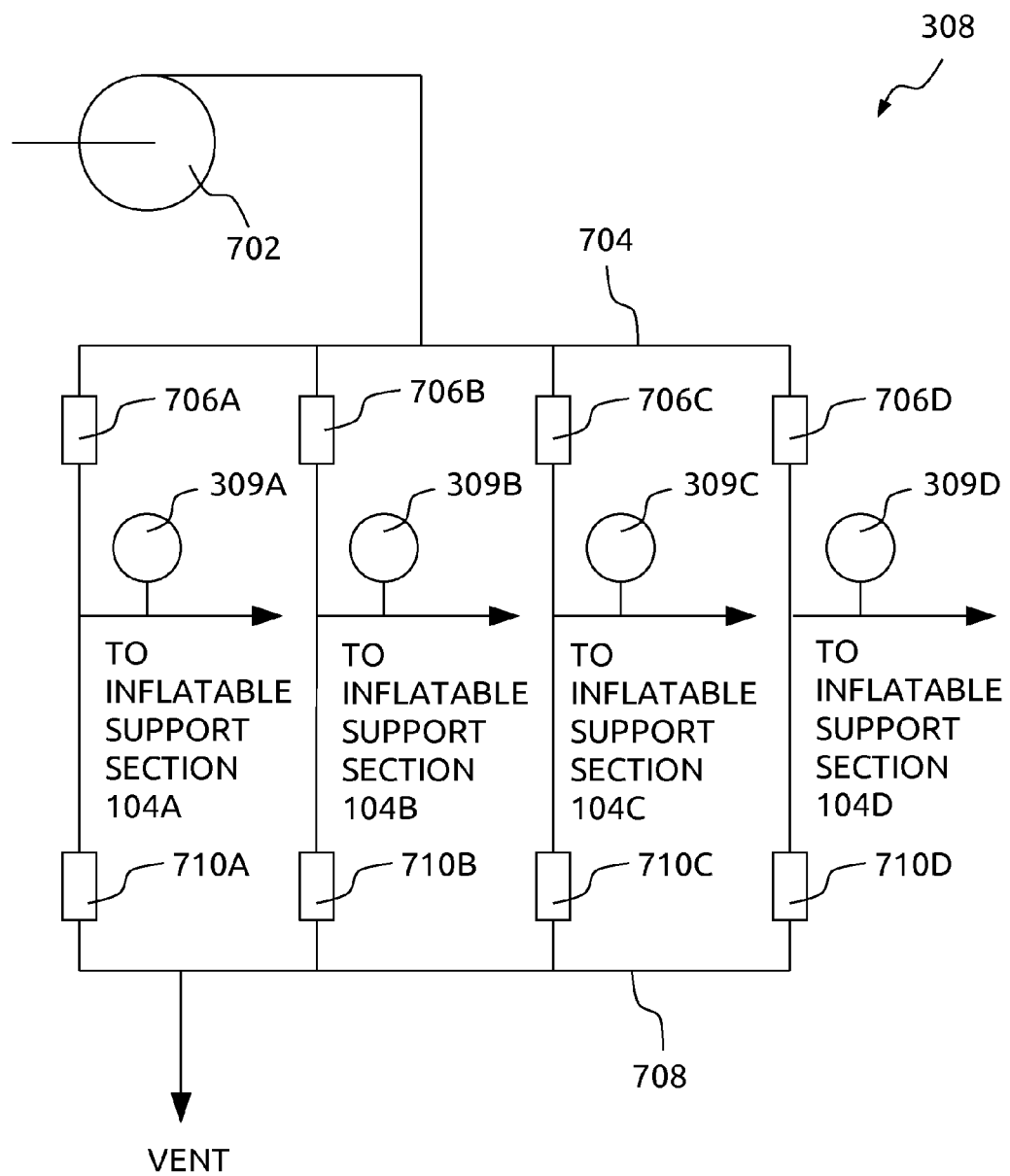
FIG. 12 is a block diagram of an example inflation system.

FIG. 12 is a block diagram of an example inflation system 308, according to at least some embodiments of the present disclosure. Some example inflation systems 308 may be configured to be mounted within housing 302 and/or may comprise conduits connectable to inflatable support sections 104A, 104B, 104C, 104D, such as via connectors 114A, 114B, 114C, 114D on external connection panel 114 (FIG. 3). In some example embodiments, a pump 702 (e.g., a 12 VDC pump) may deliver air to a supply manifold 704, which may supply air to a plurality of pump solenoid valves 706A, 706B, 706C, 706D. An individual solenoid valve 706A, 706B, 706C, 706D may be opened or shut (e.g., based on a control signal from processor 306) to deliver air to one inflatable support section 104A, 104B, 104C, 104D, when desired. Similarly, an exhaust manifold 708 may be configured to exhaust air from inflatable support sections 104A, 104B, 104C, 104D when desired via individual exhaust solenoid valves 710A, 710B, 710C, 710D associated with individual inflatable support sections 104A, 104B, 104C, 104D, respectively. Individual inflatable support sections 104A, 104B, 104C, 104D may be fluidicly connected to supply manifold 704 and/or exhaust manifold 708 via tubing or other conduit, which may include pressure sensors 309A, 309B, 309C, 309D. Pump 702, pump solenoid valves 706A, 706B, 706C, 706D, exhaust solenoid valves 710A, 710B, 710C, 710D, and/or pressure sensors 309A, 309B, 309C, 309D may be operatively connected to processor 306.

In some example embodiments, pressure sensors 309A, 309B, 309C, 309D may transmit a voltage signal from 0.5 VDC-1.5 VDC proportional to the air pressure within the respective inflatable support section 104A, 104B, 104C, 104D. This pressure signal may be amplified and sent to a processor which converts the signal to a numerical value between 1 and 1000, for example, for use in control and monitoring operations as described elsewhere herein.

Some example control units 300 may be configured to provide predictive bed-exit alarm functions. For example, unloaded pressures in inflatable support sections 104A, 104B, 104C, 104D may be measured (e.g., using pressure sensors 309A, 309B, 309C, 309D) without the patient on support structure 100. The patient may be placed on support structure 100 and loaded pressures in inflatable support sections 104A, 104B, 104C, 104D may be measured. Pressures in inflatable support sections 104A, 104B, 104C, 104D may be continuously and/or periodically measured. Processor 306 may be programmed as an alarm logic to initiate a predictive bed-exit alarm sequence when at least one inflatable support section 104A, 104B, 104C, 104D is measured at about its unloaded pressure, which may indicate that the patient has narrowed his or her footprint on support structure 100 in an attempt to exit the bed. In some example embodiments, the alarm logic may initiate the predictive bed-exit alarm sequence when at least two of inflatable support sections 104A, 104B, 104C, 104D are measured at about their unloaded pressures. By providing a predictive alarm (e.g., an alarm that is triggered before the patient has left the bed) some example embodiments may allow caregivers to intervene to prevent the patient from exiting the bed, rather than responding once the patient has already left the bed.

Some example bed-exit alarm sequences may include playing a prerecorded audible message, such as using a speaker of alert device 314. Some example control devices 300 may allow customized recording of such recorded messages, such as using microphone 313. For example, a relative of a patient may record, "Grandma, please stay in your bed." In some example embodiments, before and/or after the prerecorded audible message is played during the alarm sequence, a local audible alarm (a beep, buzzer, tone, etc.) and/or a visible alarm may be activated. Some example embodiments may include transmitting an alarm signal to a remote receiver, such as external communication device 604 (FIG. 1), which may comprise a handheld unit, a nurses station, etc.

In some example embodiments, infrared sensors (e.g., electric eyes) may be positioned along the lateral side edges of the bed generally parallel with the longitudinal axis of the bed, such as approximate the bed rails. For example, such sensors may be mounted to the headboard and/or footboard of the bed. These sensors may be utilized to detect a patient exiting the bed and/or may be utilized in connection with other bed-exit-related data to provide a bed-exit alarm.

Some example bed-exit alarm user interfaces may include enable/disable button(s), a calibration button (pressed to obtain initial pressure readings before the patient is placed on the bed), and/or a pause button (which may temporarily suspend operation of the bed exit alarm to allow a patient to leave the bed without triggering the alarm). In some example embodiments, the bed-exit alarm may be automatically re-enabled after being paused upon detecting that the patient has returned to the bed, such as by detection of loaded pressures in at least some of inflatable support sections 104A, 104B, 104C, 104D.

Some example control units 300 may be configured to provide patient weighing functions. For example, processor 306 of control unit 300 may be programmed as patient weighing logic to receive data associated with a pressure of an inflatable mat 201, such as from pressure sensor 260. Processor 306 may be programmed to detect a difference between an unloaded pressure of inflatable mat 201 and a loaded pressure of inflatable mat 201. Processor 306 may be programmed to output a patient weight corresponding to the difference between the unloaded pressure and the loaded pressure. For example, the patient weight may be indicated on display 304.

In some example embodiments, inflatable mat 201 may be inflated to a predetermined unloaded pressure (e.g., using a handheld inflator), which may be greater than atmospheric pressure. In some example embodiments, support structure 100 may be placed in a generally horizontal position prior to sensing the loaded pressure. Some example embodiments may display one or more previously obtained patient weights and/or an indication of whether the patient's weight has increased or decreased since the previous weight measurement.

Some example control units 300, such as those incorporating LCDs and/or touch screens, may provide various pages for interacting with users. For example, a "home" page may include one or more button which may be used to switch to mode pages. For example, a home page may include an inflate/deflate button, a bed exit alarm button, a scale button, a low air loss button, and/or other buttons associated with other functions. Some example mode pages may include a button for returning the screen to the home page. Some example home pages may also display various data, such as angle of the head of the bed, interface temperature, and/or interface humidity, all of which may be measured as described elsewhere herein.

An example inflate/deflate page may display current pressure readings from individual inflatable support sections 104A, 104B, 104C, 104D. Buttons may direct inflation and/or deflation of individual inflatable supports 104A, 104B, 104C, 104D using inflation system 308. In some example embodiments, processor 306 may be configured to allow user-directed inflation and/or deflation of inflatable supports 104A, 104B, 104C, 104D while preventing deflation of inflatable supports 104A, 104B, 104C, 104D such that the patient exceeds the minimum threshold for bottoming out as detected by proximity sensor mat 202. Some example embodiments may include an animated illustration of the inflation and/or deflation when such operations occur.

An example scale page may include a calibrate button (to be pressed without the patient in the bed), a current weight button (which may display the weight of the patient), and/or a kg/lb button which may toggle the measurement units. Some example embodiments may also display one or more previously obtained patient weights and/or an indication of whether the patient's weight has increased or decreased since the previous weight measurement.

An example low air loss page may include buttons allowing activation and deactivation of a low air loss air supply and/or adjustment of the low air loss air supply. Some example embodiments may include display of the volumetric flow rate of air provided by the low air loss air supply.

Figure 13:
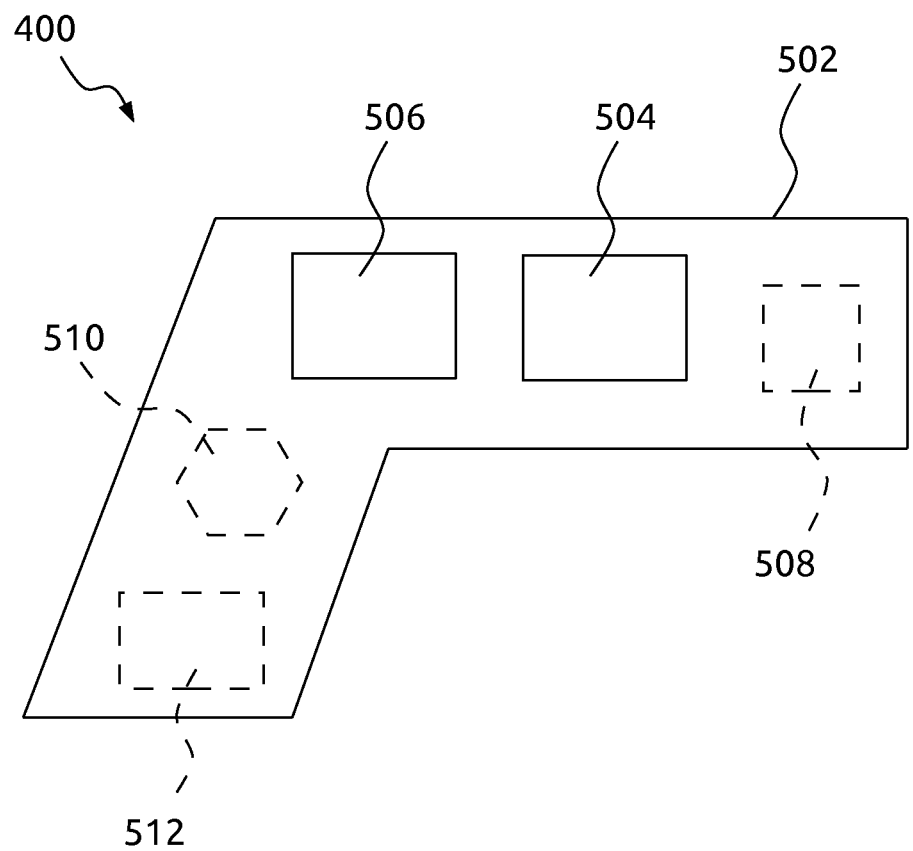
FIG. 13 is a block diagram of an example handheld control unit.

FIG. 13 is a block diagram of an example handheld control unit 400, according to at least some embodiments of the present disclosure. Handheld control unit 400 may comprise control unit 300 (FIG. 1) and/or may be configured to be readily portable. For example, handheld control unit 400 may be carried from bed to bed to monitor and/or adjust inflatable supports 104 periodically and/or as desired. For example, handheld control unit 400 may be configured generally in the form of a cordless drill or other readily portable, battery-powered device. In an example embodiment, a housing 502 may receive a display 504 (e.g., an LCD), a user interface 506 (e.g., one or more membrane switches), an inflation system 508 (e.g., a pump and/or a pressure sensor), and/or a processor 510 (which may include memory), all of which may be powered from a battery 512.

Some example handheld control units 400 may be configured to assist a user with setup operations associated with support structure 100. For example, processor 510 may be programmed to ask the user for the patient's height and/or weight. The user may enter the patient's height and/or weight, and processor 510 may determine an appropriate unloaded inflation pressure for individual inflatable support sections 104A, 104B, 104C, 104D. The user may connect inflation system 508 to inflatable support section 104A, handheld control unit 400 may determine the current pressure in inflatable support section 104A, and/or may inflate or vent air as necessary to achieve the desired pressure. This process may be repeated for inflatable support sections 104B, 104C, 104D. In some example embodiments, handheld control unit 400 may ask the user whether the patient is lying on support structure 100 and, if so, handheld control unit 400 may adjust inflatable support sections 104A, 104B, 104C, 104D to appropriate loaded pressures.

Some example embodiments may be configured to store and/or retrieve data associated with a plurality of support structures 100. For example, an example handheld control unit 400 may store data (e.g., desired pressures) for a plurality of support structures designated by support structure numbers or other identifiers. A caregiver may enter the support structure number into handheld control unit 400, and handheld control unit 400 may retrieve the previously stored data associated with that support structure. Some example embodiments may be configured to transmit and/or receive data.

Some example control units 300 may be configured to transmit and/or receive data from a remote location. For example, alarms and measured parameters may be communicated to a nurses station and/or a remote facility. For example, an example embodiment may notify a nurses station upon detecting a patient attempting to exit a bed. Some example embodiments may be configured to respond to commands (e.g., inflate or deflate particular inflatable supports 104A, 104B, 104C, 104D) received from remote locations. Some example embodiments may include one or more speakers and/or microphones to allow voice communication with a remote location (e.g., via voice-over-IP (VoIP)). For example, a provider of a patient support system 10 may utilize such voice communication capability to walk a user through a setup or troubleshooting procedure. Some example embodiments may be configured to receive software and/or firmware updates via the Internet, for example.

Some example embodiments may be configured to record and store data. For example, control unit 300 may store data associated with usage, such as the number of hours that such control unit 300 is utilized in connection with support structure 100. Such usage data may be transmitted and/or downloaded to allow usage-based billing, such as on a partial-day or hourly basis. It is contemplated that such usage based billing may be used, for example, where a medical facility purchases a plurality of support structures 100 and a smaller number of control units 300. Such control units 300 may be stored at the medical facility and may be used as necessary. The medical facility may be billed for control units 300 based on the number of hours use, which may be recorded and transmitted to the patient support system supplier by control units 300. For example, control units 300 may transmit usage data each month to allow billing of the medical facility.

Some example embodiments may be configured to record data for purposes other than billing. For example, certain variations in detected pressures of inflatable supports 104A, 104B, 104C, 104D may be associated with a patient being turned (e.g., from one side to the other side), such as may be performed to reduce the risk of pressure sores. Data related to such turnings may be stored to provide a record that turning procedures were properly carried out by nursing staff. Similarly, temperature, humidity, and other data may be used to show that proper pressure-sore-preventative procedures were conducted. As another example, data associated with the angle of the bed, pressures of inflatable supports 104A, 104B, 104C, 104D, etc., may be accessed in an investigation related to a patient fall.

Some example embodiments may be configured to allow tracking of components, such as support structures 100, mats 200, and/or control units 300. For example, control units 300 including data transmitting capabilities may be configured to report their locations to a remote facility. Some example embodiments may be provided with tracking devices, such as radio frequency identification tags, which may allow improved tracking and/or inventory management.

In some example embodiments a printed circuit board (PCB) may operatively connect the processor and one or more sensors, solenoid valves, and/or any other data input and/or controlled components. For example a PCB may be connected to the processor using a USB interface. An example PCB may include USB communication modules, one or more potentiometers, one or more amplifiers, and/or appropriate wiring to connect the various components.

FIG. 14 is a flowchart of an example method 2000 of operating a patient support system. Method 2000 may comprise operation 2002, which may comprise placing a patient on a substantially vapor-permeable top cover of a support structure. The support structure may comprise a generally rectangular base comprising a top surface, a first longitudinally oriented sidewall and a second longitudinally oriented sidewall extending upward from lateral side portions of the base, and a substantially vapor-impermeable barrier disposed on the top surface of the base and on inwardly facing surfaces of the first longitudinally oriented sidewall and the second longitudinally oriented sidewall, and an inflatable support. The vapor-permeable top cover may extend between upper aspects of the first longitudinally oriented sidewall and the second longitudinally oriented sidewall such that a generally longitudinally oriented channel configured to receive airflow therethrough is substantially defined by a lower surface of the top cover, an upper surface of the barrier on the base, and inwardly facing surfaces of the barrier on the first longitudinally oriented sidewall and the second longitudinally oriented sidewall. The inflatable support may be disposed in the channel, and an interior volume of the inflatable support may be fluidicly isolated from channel. Operation 2002 may be followed by operation 2004, which may include flowing air through the channel while the patient is on the substantially vapor-permeable top cover.

Figure 15:
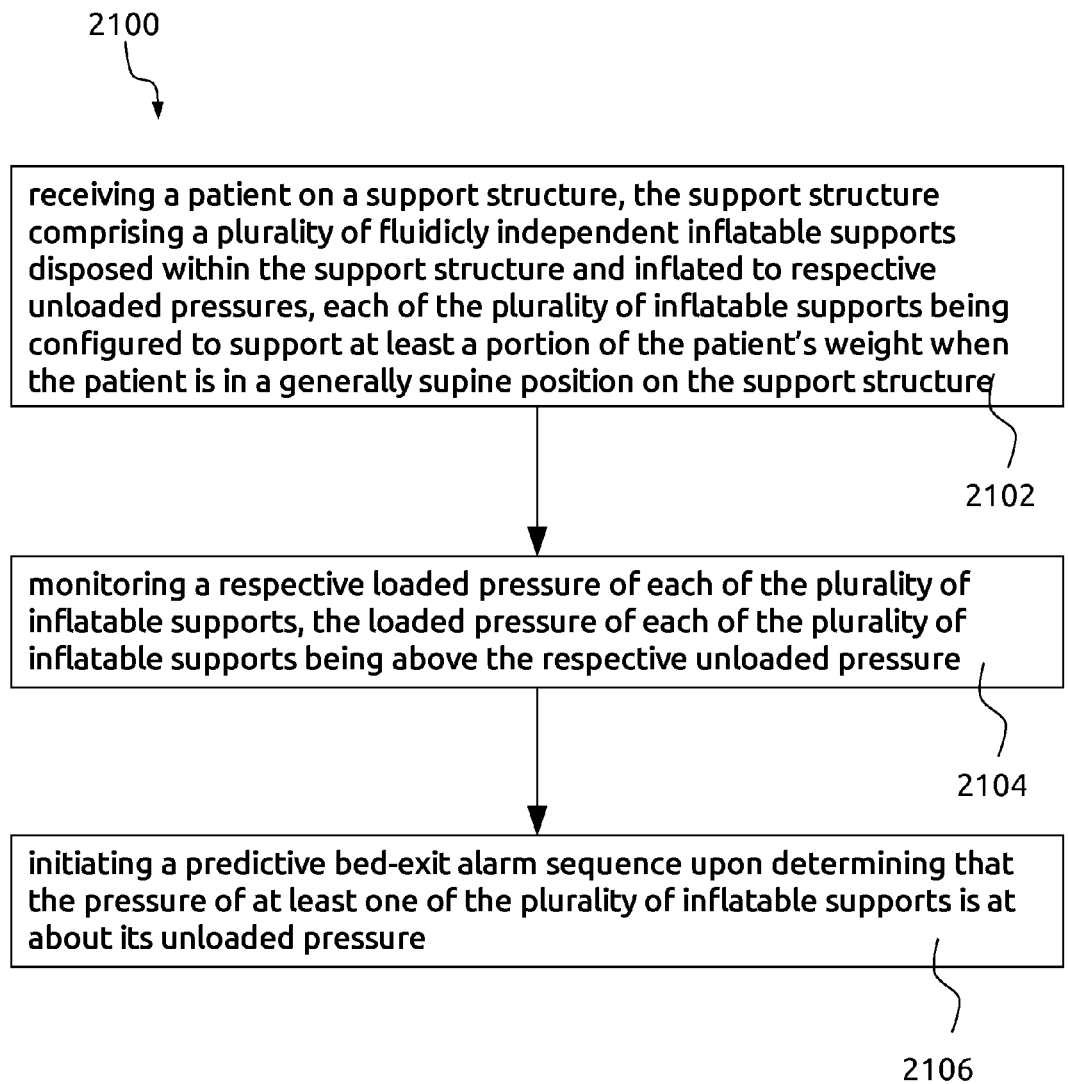
FIG. 15 is a flowchart of an example method of providing a predictive bed-exit alarm.

FIG. 15 is a flowchart of an example method 2100 of providing a predictive bed-exit alarm. Method 2100 may comprise operation 2102, which may comprise receiving a patient on a support structure. The support structure may comprise a plurality of fluidicly independent inflatable supports disposed within the support structure and inflated to respective unloaded pressures. Each of the plurality of inflatable supports may be configured to support at least a portion of the patient's weight when the patient is in a generally supine position on the support structure. Operation 2102 may be followed by operation 2104, which may include monitoring a respective loaded pressure of each of the plurality of inflatable supports. The loaded pressure of each of the plurality of inflatable supports may be above the respective unloaded pressure. Operation 2104 may be followed by operation 2106, which may include initiating a predictive bed-exit alarm sequence upon determining that the pressure of at least one of the plurality of inflatable supports is at about its unloaded pressure.

Figure 16:
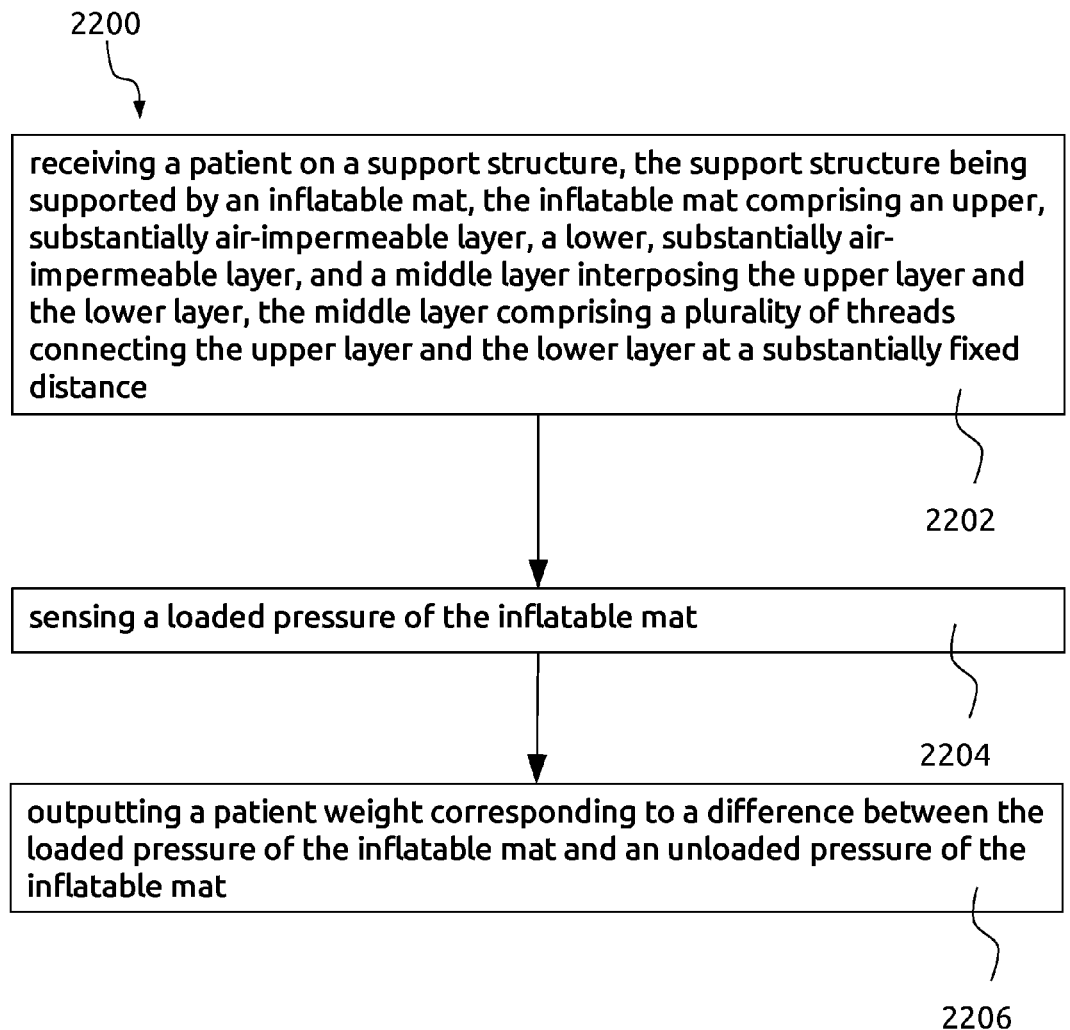
FIG. 16 is a flowchart of an example method of determining a patient weight.

FIG. 16 is a flowchart of an example method 2200 of determining a patient weight. Method 2200 may include operation 2202, which may include receiving a patient on a support structure. The support structure may be supported by an inflatable mat. The inflatable mat may comprise an upper, substantially air-impermeable layer, a lower, substantially air-impermeable layer, and a middle volume interposing the upper layer and the lower layer. The middle volume may comprise a plurality of threads connecting the upper layer and the lower layer at a substantially fixed distance. Operation 2202 may be followed by operation 2204, which may include sensing a loaded pressure of the inflatable mat. Operation 2204 may be followed by operation 2206, which may include outputting a patient weight corresponding to a difference between the loaded pressure of the inflatable mat and an unloaded pressure of the inflatable mat.

Figure 17:
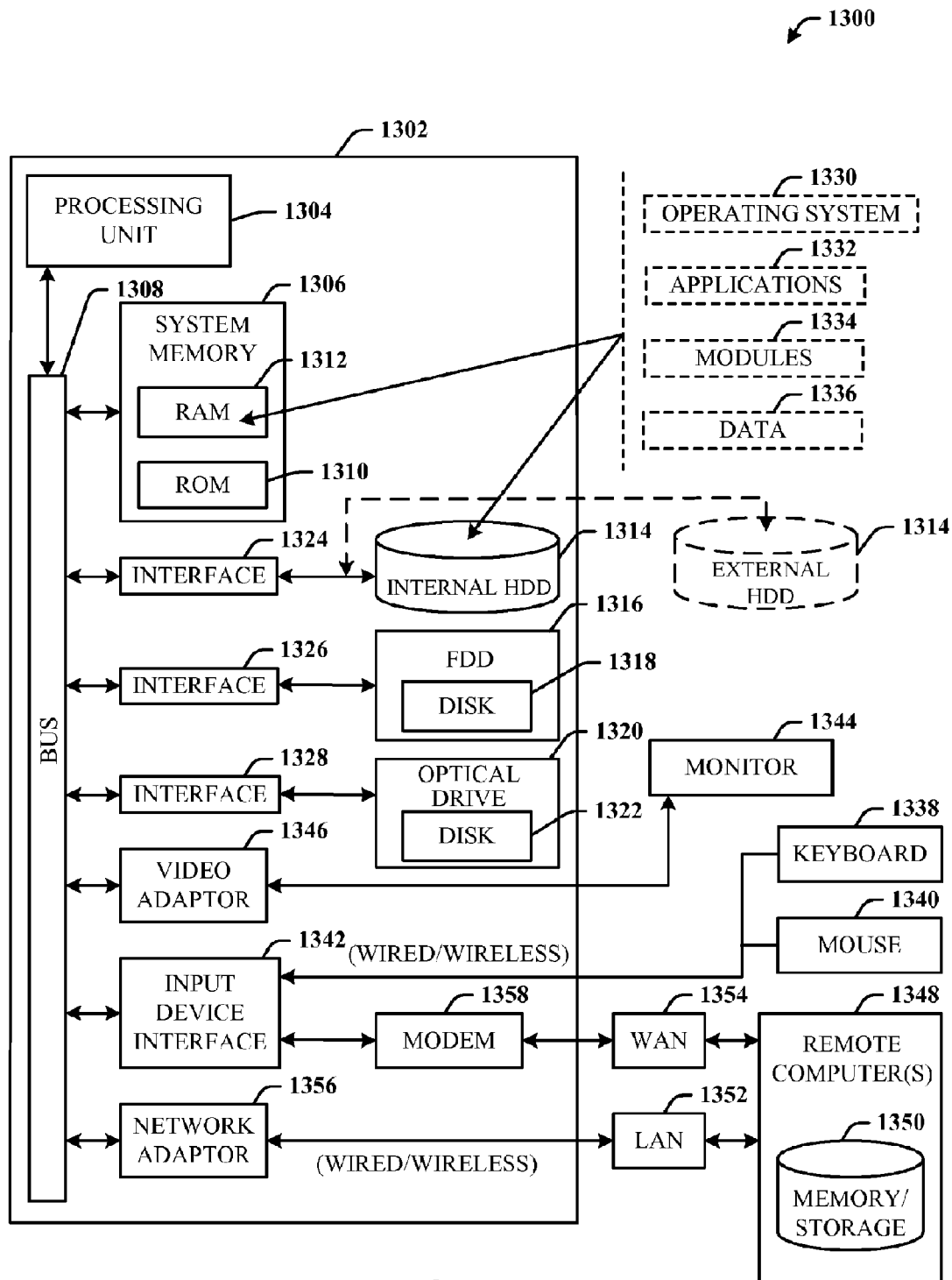
FIG. 17 is a block diagram of an example computer; all arranged in accordance with at least some embodiments of the present disclosure.

FIG. 17 is a block diagram of an example computer. In order to provide additional context for various aspects of the present disclosure, the following discussion provides a brief, general description of a computing environment 1300. Those skilled in the art will recognize that the various aspects of the present disclosure may be implemented in combination with other program modules and/or as a combination of hardware and software.

Generally, program modules include routines, programs, components, data structures, etc., that perform particular tasks or implement particular abstract data types. Moreover, those skilled in the art will appreciate that the methods according to the present disclosure may be practiced with other computer system configurations, including single-processor or multiprocessor computer systems, minicomputers, mainframe computers, as well as personal computers, handheld computing devices, microprocessor-based or programmable consumer electronics, and the like, each of which can be operatively coupled to one or more associated devices.

Some aspects of the present disclosure may also be practiced in distributed computing environments where certain tasks are performed by remote processing devices that are linked through a communications network. In some example distributed computing environments, program modules may be located in local and/or remote memory storage devices.

An example computer may include a variety of computer-readable media. Computer-readable media may include any available media that can be accessed by the computer and includes both volatile and non-volatile media, as well as removable and non-removable media. By way of example, and not limitation, computer-readable media may comprise computer storage media and communication media. Computer storage media may include volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the computer.

An example computing environment 1300 for implementing various aspects includes a computer 1302, which may include a processing unit 1304, a system memory 1306 and/or a system bus 1308. The system bus 1308 may couple system components including, but not limited to, the system memory 1306 to the processing unit 1304. The processing unit 1304 can be any of various commercially available processors. Dual microprocessors and other multi-processor architectures may also be employed as the processing unit 1304.

The system bus 1308 can be any of several types of bus structures that may further interconnect to a memory bus (with or without a memory controller), a peripheral bus, and/or a local bus using any of a variety of commercially available bus architectures. The system memory 1306 may include read only memory (ROM) 1310 and/or random access memory (RAM) 1312. A basic input/output system (BIOS) may be stored in a non-volatile memory 1310 such as ROM, EPROM, EEPROM. BIOS may contain basic routines that help to transfer information between elements within the computer 1302, such as during start-up. The RAM 1312 can also include a high-speed RAM such as static RAM for caching data.

The computer 1302 may further include an internal hard disk drive (HDD) 1314 (e.g., EIDE, S ATA), which may also be configured for external use in a suitable chassis, a magnetic floppy disk drive (FDD) 1316 (e.g., to read from or write to a removable diskette 1318), and/or an optical disk drive 1320 (e.g., reading a CD-ROM disk 1322 or, to read from or write to other high capacity optical media such as the DVD). The hard disk drive 1314, magnetic disk drive 1316, and/or optical disk drive 1320 can be connected to the system bus 1308 by a hard disk drive interface 1324, a magnetic disk drive interface 1326, and an optical drive interface 1328, respectively. The interface 1324 for external drive implementations may include at least one or both of Universal Serial Bus (USB) and IEEE 1394 interface technologies. Other external drive connection technologies are within the scope of the disclosure.

The drives and their associated computer-readable media may provide nonvolatile storage of data, data structures, computer-executable instructions, and so forth. For the computer 1302, the drives and media may accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in an example operating environment, and further, that any such media may contain computer-executable instructions.

A number of program modules can be stored in the drives and RAM 1312, including an operating system 1330, one or more application programs 1332, other program modules 1334, and/or program data 1336. All or portions of the operating system, applications, modules, and/or data can also be cached in the RAM 1312. It is to be appreciated that various commercially available operating systems or combinations of operating systems may be utilized.

A user can enter commands and information into the computer 1302 through one or more wired/wireless input devices, e.g., a keyboard 1338 and a pointing device, such as a mouse 1340. Other input devices may include a microphone, an IR remote control, a joystick, a game pad, a stylus pen, touch screen, or the like. These and other input devices are often connected to the processing unit 1304 through an input device interface 1342 that is coupled to the system bus 1308, but can be connected by other interfaces, such as a parallel port, an IEEE 1394 serial port, a game port, a USB port, an IR interface, etc.

A monitor 1344 or other type of display device may also connected to the system bus 1308 via an interface, such as a video adapter 1346. In addition to the monitor 1344, a computer typically includes other peripheral output devices, such as speakers, printers, etc.

The computer 1302 may operate in a networked environment using logical connections via wired and/or wireless communications to one or more remote computers, such as a remote computer(s) 1348. The remote computer(s) 1348 can be a workstation, a server computer, a router, a personal computer, portable computer, microprocessor based entertainment appliance, a peer device, and/or other common network node, and/or may include many or all of the elements described relative to the computer 1302, although, for purposes of brevity, only a memory/storage device 1350 is illustrated. The logical connections depicted include wired/wireless connectivity to a local area network (LAN) 1352 and/or larger networks, e.g., a wide area network (WAN) 1354. Such LAN and WAN networking environments are commonplace in offices and health care facilities, and facilitate enterprise-wide computer networks, such as intranets, all of which may connect to a global communications network, e.g., the Internet.

When used in a LAN networking environment, the computer 1302 may be connected to the local network 1352 through a wired and/or wireless communication network interface or adapter 1356. The adaptor 1356 may facilitate wired or wireless communication to the LAN 1352, which may also include a wireless access point disposed thereon for communicating with the wireless adaptor 1356.

When used in a WAN networking environment, the computer 1302 can include a modem 1358, or may be connected to a communications server on the WAN 1354, or may have other devices for establishing communications over the WAN 1354, such as by way of the Internet. The modem 1358, which can be internal or external and a wired or wireless device, may be connected to the system bus 1308 via the serial port interface 1342. In a networked environment, program modules depicted relative to the computer 1302, or portions thereof, can be stored in the remote memory/storage device 1350. It will be appreciated that the network connections shown are exemplary and other means of establishing a communications link between the computers can be used.

The computer 1302 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag, and/or telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11x (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks can operate in the unlicensed 2.4 and 5 GHz radio bands. IEEE 802.11 applies to generally to wireless LANs and provides 1 or 2 Mbps transmission in the 2.4 GHz band using either frequency hopping spread spectrum (FHSS) or direct sequence spread spectrum (DSSS). IEEE 802.11a is an extension to IEEE 802.11 that applies to wireless LANs and provides up to 54 Mbps in the 5 GHz band. IEEE 802.1a uses an orthogonal frequency division multiplexing (OFDM) encoding scheme rather than FHSS or DSSS. IEEE 802.11b (also referred to as 802.11 High Rate DSSS or Wi-Fi) is an extension to 802.11 that applies to wireless LANs and provides 11 Mbps transmission (with a fallback to 5.5, 2 and 1 Mbps) in the 2.4 GHz band. IEEE 802.11g applies to wireless LANs and provides 20+ Mbps in the 2.4 GHz band. Products can operate in more than one band (e.g., dual band), so the networks can provide real-world performance similar to the basic 10BaseT wired Ethernet networks used in many offices.

All dimensions provided herein are merely examples and are not to be considered limiting.

While example embodiments have been set forth above for the purpose of disclosure, modifications of the disclosed embodiments as well as other embodiments thereof may occur to those skilled in the art. Accordingly, it is to be understood that the disclosure is not limited to the above precise embodiments and that changes may be made without departing from the scope. Likewise, it is to be understood that it is not necessary to meet any or all of the stated advantages or objects disclosed herein to fall within the scope of the disclosure, since inherent and/or unforeseen advantages may exist even though they may not have been explicitly discussed herein.

What is claimed is:

1. A patient support system comprising:
    a generally rectangular base comprising a top surface;
    a first longitudinally oriented sidewall and a second longitudinally oriented sidewall extending upward from lateral side portions of the base;
    a substantially vapor-impermeable barrier disposed on the top surface of the base and on inwardly facing surfaces of the first longitudinally oriented sidewall and the second longitudinally oriented sidewall;
    a top cover extending between upper aspects of the first longitudinally oriented sidewall and the second longitudinally oriented sidewall such that a generally longitudinally oriented channel configured to receive airflow therethrough is substantially defined by a lower surface of the top cover, an upper surface of the barrier on the base, and inwardly facing surfaces of the barrier on the first longitudinally oriented sidewall and the second longitudinally oriented sidewall;
    a supply conduit extending from an exterior air supply connector to an internal air supply opening within the channel at a first longitudinal end of the base;

an air discharge opening within the channel, positioned at a second longitudinal end of the base opposing the first longitudinal end, the air discharge opening being arranged to allow air to exit the channel;

an inflatable support layer disposed in the channel, the inflatable support layer being composed of at least two sections corresponding to a respective two portions of a patient's body, each section being separately inflatable and deflatable, and each section being fluidicly isolated from each other section, each section including an array of upstanding, inflatable supports having interior volume;

a control unit operatively configured to inflate and vent air from each of the at least two sections; and an air source separate from the control unit, fluidicly coupled to the exterior air supply connector, for providing an airflow through the channel in a longitudinal direction from the first longitudinal end to the second longitudinal end, and around the arrays of upstanding, inflatable supports comprising the at least two sections of the inflatable support layer;

wherein the interior volume of the inflatable supports is fluidicly isolated from the channel.

2. The patient support system of claim 1, wherein the first longitudinally oriented sidewall and the second longitudinally oriented sidewall are disposed on lateral side portions of the top surface of the base.

3. The patient support system of claim 1, wherein the first longitudinally oriented sidewall and the second longitudinally oriented sidewall are disposed against outwardly facing lateral side edges of the base.

4. The patient support system of claim 1, wherein the first longitudinally oriented sidewall and the second longitudinally oriented sidewall are integrally formed with the base.

5. The patient support system of claim 1, further comprising a head end wall extending upward from a head end portion of the base and extending laterally from the first longitudinally oriented sidewall to the second longitudinally oriented sidewall.

6. The patient support system of claim 5, wherein the head end wall comprises the air discharge opening.

7. The patient support system of claim 1, wherein the air discharge opening is vented to an ambient environment.

8. The patient support system of claim 7, wherein the air discharge opening is vented to the ambient environment through a filter.

9. The patient support system of claim 8, wherein the filter comprises a mesh screen.

10. The patient support system of claim 8, wherein the filter comprises a stainless steel mesh of about 44 microns.

11. The patient support system of claim 1, wherein the internal air supply opening is disposed within the channel approximate a foot end of the generally rectangular base.

12. The patient support system of claim 1, wherein the air discharge opening is disposed within the channel approximate a head end of the generally rectangular base.

13. A method of operating a patient support system, the method comprising:

placing a patient on a top cover of a support structure, the support structure comprising a generally rectangular base comprising a top surface, a first longitudinally oriented sidewall and a second longitudinally oriented sidewall extending upward from lateral side portions of the base, a substantially vapor-impermeable barrier disposed on the top surface of the base and on inwardly facing surfaces of the first longitudinally oriented sidewall and the second longitudinally oriented sidewall, and an inflatable support layer, wherein the vapor-permeable top cover extends between upper aspects of the first longitudinally oriented sidewall and the second longitudinally oriented sidewall such that a generally longitudinally oriented channel configured to receive airflow therethrough is substantially defined by a lower surface of the top cover, an upper surface of the barrier on the base, and inwardly facing surfaces of the barrier on the first longitudinally oriented sidewall and the second longitudinally oriented sidewall, wherein the inflatable support is disposed in the channel and is composed of at least two sections corresponding to a respective two portions of a patient's body, each section being separately inflatable and deflatable, and each section being fluidicly isolated from the other section, and each section including an array of upstanding, inflatable supports having an interior volume, and wherein the interior volume of the inflatable supports is fluidicly isolated from the channel;

selectively controlling inflation of the at least two sections based upon sensor data associated with the support structure; and flowing air through the channel from one longitudinal end of the support structure to an opposing longitudinal end of the support structure and around the arrays of upstanding, inflatable supports while the patient is on the top cover.

14. The method of claim 13, wherein placing the patient on the top cover includes placing at least one article at least partially interposing the patient and the top cover.

15. The method of claim 13, wherein flowing air through the channel comprises supplying air via a supply conduit extending from an exterior air supply connector to an internal air supply opening within the channel; and exhausting air from the channel via an air discharge opening within the channel.

16. The method of claim 15, wherein supplying air via the supply conduit comprises coupling an air source to the exterior air supply connector.

* * * * *